United States Patent [19]

Brain

[11] Patent Number: 4,826,820
[45] Date of Patent: May 2, 1989

[54] 6-CARBAMADE ERYTHROMYCIN DERIVATIVES

[75] Inventor: Edward G. Brain, Betchworth, England

[73] Assignee: Beecham Group p.l.c., England

[21] Appl. No.: 900,364

[22] Filed: Aug. 26, 1986

[30] Foreign Application Priority Data

Aug. 28, 1985 [GB] United Kingdom ............... 8521402

[51] Int. Cl.$^4$ ..................... A61K 31/70; C07H 17/08
[52] U.S. Cl. ...................... 514/29; 536/7.2; 536/7.4
[58] Field of Search ............. 536/7.2, 7.4; 514/29

[56] References Cited

U.S. PATENT DOCUMENTS 4,133,950  1/1979  Myers ................................ 536/7.4

OTHER PUBLICATIONS

Morrison et al., *Organic Chemistry*, 3rd ed., Allyn and Bacon, Inc., 1973, p. 1044.
The Merck Index, 10th Edition, 1983, pp. 531-532, Ref. No. 3624, "Erythromycin"; Merck & Co., Inc., Rahway, N.J., U.S.

*Primary Examiner*—Johnnie R. Brown
*Assistant Examiner*—Elli Peselev
*Attorney, Agent, or Firm*—Jacobs & Jacobs

[57] ABSTRACT

Antibacterially active 6-carbamate erythromycin derivatives of formula I and their pharmaceutically acceptable esters and acid addition salts;

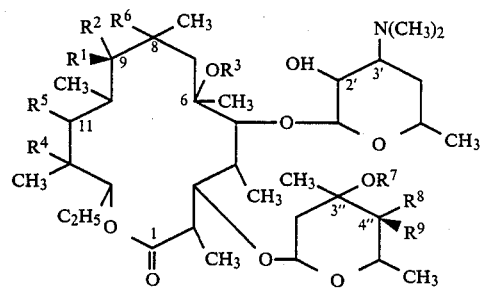

wherein:
$R^1$ or $R^2$ is optionally substituted amino, or $R^1$ or $R^2 + R^5$ is —O—C($R^A$)($R^B$)—O—, and $R^2$ or $R^1$ is H, or $R^1 + R^2$ is oxo, oxime, substituted oxime, or imino;
$R^3$ is carbamoyl or N-substituted carbamoyl;
$R^4$ is H or OH, and $R^5$ is OH, or etherified hydroxy, or $R^4 + R^5$ is —O—CO—O— or —O—C($R^A$)($R^B$)—O—;
$R^6$ is H, F or OH;
$R^7$ is H or $CH_3$;
$R^8$ or $R^9$ is H, OH, alkoxy, optionally substituted $NH_2$, alkanoyloxy, or $R^C$—$SO_2O$—, and $R^9$ or $R^8$ is H, or $R^8 + R^9$ is oxo or optionally substituted oxime;
$R^A$, $R^B$ are H or hydrocarbon; and
$R^C$ is organic.

24 Claims, No Drawings

6-CARBAMADE ERYTHROMYCIN DERIVATIVES

The present invention relates to novel chemical compounds, their preparation and their use, and in particular to a novel class of erythromycin derivatives. These compounds have antibacterial properties, in particular against Gram-positive bacteria but also against some Gram-negative bacteria, and they are therefore of use in the treatment of bacterial infections in humans and animals caused by a wide range of organisms.

Erythromycin was first described in U.S. Pat. No. 2,653,899 (R. L. Bunch et al; Eli Lilly). The structure of erythromycins can be represented as follows:

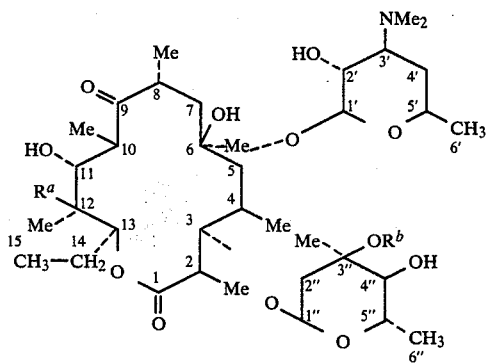

in which
$R^a$ denotes hydrogen or hydroxy and
$R^b$ denotes hydrogen or methyl.

The basic erythromycin structure comprises:
(i) a 14-membered lactone ring, referred to as the erythronolide ring, numbered with unprimed digits as shown in the above formula,
(ii) a first sugar ring, known as the desosamine ring, numbered with single-primed digits, and
(iii) a second sugar ring, known as the cladinose ring, numbered with double-primed digits.

The erythronolide ring can exist in two forms:
erythronolide A (in which $R^a$=OH)
erythronolide B (in which $R^a$=H).

The four main naturally occurring erythromycins are as follows:

| Erythromycin | $R^a$ | $R^b$ |
|---|---|---|
| A | OH | CH$_3$ |
| B | H | CH$_3$ |
| C | OH | H |
| D | H | H | of which erythromycin A is by far the most important. Erythromycins, and in particular erythromycin A, are antibiotics widely employed clinically in the treatment of infections caused by Gram-positive and some Gram-negative bacteria. A major drawback of erythromycins is their poor acid stability, resulting in poor and erratic oral absorption.

Numerous attempts have been made to modify erythromycin to produce derivatives having improved acid stability without loss of the antibacterial activity.

(9S)-9-Dihydroerythromycin A (which carries a 9-hydroxy group in place of the 9-keto group) has been described, but has poor antibacterial activity (P. F. Wiley et al, *J. Amer. Chem. Soc.,* 1955, 77, 3676–3677; M. V. Sigal et al, ibid, 1956, 78, 388–395; and T. Glabski et al, *Roczniki Chem.,* 1976, 50, 1281). Erythromycylamine and erythromycin oxime (in which the 9-keto group is replaced, respectively, by an amino or oxime group), as well as various N-substituted derivatives of erythromycylamine have also been described (GB 1 100 504 (Pliva Pharmaceutical); E. H. Massey et al, *Tetrahedron Letters,* 1970, No. 2, 157–160; and G. H. Timms et al, ibid, 1971, No. 2, 195–198), as have various erythromycin oxime ethers (U.S. Pat. No. 3,681,326 (A. M. Von Esch; Abbott Laboratories); U.S. Pat. No. 3,869,445 and 4,063,014 (both R. Hallas et al; Abbott Laboratories); U.S. Pat. No. 4,349,545 (S. Gouin d'Ambrieres; Roussel-Uclaf)); and *Antimicrobial agents and chemotherapy,* 1974, 6 479).

Certain aldehyde-erythromycylamine condensation products with a 9-N,6-O- or 9-N,11-O-cyclic substituent have previously been disclosed (U.S. Pat. No. 4,048,306 (R. Maier et al; Boehringer Ingelheim GmbH)). 4"-Deoxy-11-O-methylthiomethyl-4"-oxo-erythromycin B and its conversion to (i) 4"-deoxy-9,11-O-(optionally substituted)methylene-4"-oxo-erythromycin B 6,9-hemiacetal and the corresponding 4"-epi-hydroxy, 2', 4"-O-diacetyl-4"-epi, and 4"-O-acetyl-4"-epi derivatives, and (ii) 4"-deoxy-4"-oxo-, 4"-O-acetyl-4"-epi-, and 4"-epi-erythromycin B; as well as 4"-O-formyl-11-O-methylthiomethyl-erythromycin B and its conversion to 11-O-methylthiomethyl-erythromycin B, 9,11-O-methylene-erythromycin B 6,9-hemiacetal, 11-O-methyl-erythromycin B and 11-O-n-butylerythromycin B; and also 4"-deoxy-4"-oxo-erythromycin A are described in U.S. Pat. Nos. 3,842,069, 3,884,903 and 3,884,904 (all P. H. Jones et al; Abbott Laboratories).

4"-Deoxy-4"-amino-erythromycin A, 4"-deoxy-4"-amino-erythromycin A 6,9-hemiketal, and 4"-deoxy-4"-oxo-erythromycin A 6,9-hemiketal, as well as corresponding 11-O-acetyl and 11,12-cyclic carbonate derivatives, and also 4"-deoxy-4"-amino-erythromycin B and 4"-deoxy-4"-oxo-erythromycin A 4"-O-oxime or 4"-O-acetyloxime, are described in U.S. Pat. No. 4,150,220 (F. C. Sciavolino; Pfizer).

Various 4"-O-sulhhonyl derivatives of erythromycin, erythromycin oxime, and erythromycin oxime ethers are described in U.S. Pat. Nos. 3,836,519, 3,869,445 and 4,063,114 (all R. Hallas et al; Abbott Laboratories). Certain further 4"-deoxy-erythromycin derivatives are described in JP No. 58-049396 (Toyo Jozo KK).

An 11,12-cyclic carbonate of 9-dihydroerythromycin has also been described in T. Glabski et al; *Roczniki Chem.,* 1976, 50, 1281 and 9-dihydro-11,12-O-isopropylidene-erythromycin A and the corresponding 4"-epi compound, as well as 4"-epi-erythromycin A and corresponding 9-dihydro, 11,12-carbonate, 9-dihydro-11,12-carbonate, and 2'-acetyl compounds, have been described in U.S. Pat. Nos. 4,382,085 and 4,382,086 (both F. C. Sciavolino et al; Pfizer).

11,12-O-(optionally substituted)-methylene derivatives and 9,11,-O-(optionally substituted)-methylene derivatives of erythromycin are described in WO No. 86/01513 and EP No. 0 184 921 A2, respectively (both Beecham).

6-O-Methyl-, 6,11-di-O-methyl-, 11-O-methyl- and 11-O-ethyl-erythromycin A, and also 6-O-methyl-6,4"-di-O-methyl-, and 6,11,4"-tri-O-methylo erythromycin B are described in EP No. 0 041 355 Al, EP No. 0 080 818 Al, EP No. 0 080 819 Al, and EP No. 0 158 467 A2 (all Taisho Pharmaceutical).

8-hydroxy-erythromycin A and 8-fluoro-erythromycin A have been described (K. Krowicki et al, *J. Antibiotics*, XXVI 575–581 (1973), and L. Toscano et al, ibid XXXVI 1439–1450 (1983), respectively). Various 6,9-ketal derivatives of 8-fluoro-erythromycins have also been described (EP No. 0 158 102 A, Pierrel).

The present invention provides antibacterially active 6-carbamate derivatives of erythromycin, and corresponding 9-(optionally substituted)oxime, 9-(optionally substituted)amino, and 9-imino compounds.

In particular, the present invention provides a compound of the general formula I or a pharmaceutically acceptable ester or acid addition salt thereof:

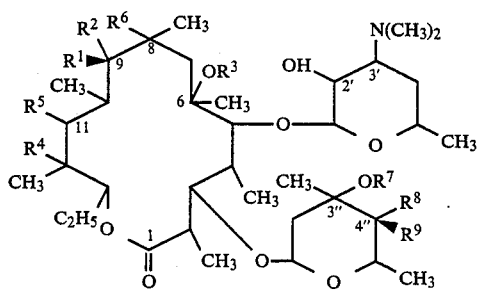

wherein one of $R^1$ and $R^2$ denotes hydrogen, and the other of $R^1$ and $R^2$ denotes an amino group or a substituted amino group, or the other of $R^1$ and $R^2$, together with $R^5$, denotes a group of the formula III below, or $R^1$ and $R^2$ together denote an oxo group, an oxime group, a substituted oxime group, or an imino group;

$R^3$ denotes a carbamoyl group or an N-substituted carbamoyl group;

$R^4$ denotes hydrogen or hydroxy, and $R^5$ denotes hydroxy, or an etherified hydroxy group, or together with $R^1$ or $R^2$ denotes a group of the formula III below as defined above, or $R^4$ and $R^5$ together denote a group of the formula II or III:

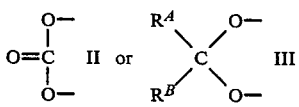

in which each of $R^A$ and $R^B$, which may be identical or different, denotes hydrogen or a hydrocarbon group;

$R^6$ denotes hydrogen, fluorine or hydroxy;

$R^7$ denotes hydrogen or methyl;

one of $R^8$ and $R^9$ denotes hydrogen, hydroxy, alkoxy, alkanoyloxy, amino, substituted amino, or a group of the formula $R^C$—$SO_2$—O—, in which $R^C$ denotes an organic group, and the other of $R^8$ and $R^9$ denotes hydrogen, or $R^8$ and $R^9$ together denote an oxo group, an oxime group, or a substituted oxime group.

The term 'hydrocarbon' as used herein includes groups having up to 18 carbon atoms, suitably up to 10 carbon atoms, conveniently up to 6 carbon atoms. Suitable hydrocarbon groups include $(C_{1-6})$alkyl, $(C_{2-6})$alkenyl, $C_{2-6}$alkynyl, $(C_{3-7})$cycloalkyl, aryl, $(C_{3-7})$cycloalkyl$(C_{1-6})$alkyl, aryl$(C_{1-6})$alkyl, $(C_{1-6})$alkyl$(C_{3-7})$cycloalkyl, and $(C_{1-6})$alkylaryl.

Examples of suitable optional substituents for the above-mentioned hydrocarbon groups include, heterocylyl, amino, $(C_{1-6})$alkanoylamino, (mono, di, or tri)-$(C_{1-6})$alkylamino, hydroxy, $(C_{1-6})$alkoxy, mercapto, $(C_{1-6})$alkylthio, heterocyclylthio, arylthio, sulphamoyl, carbamoyl, amidino, guanidino, nitro, chloro, bromo, fluoro, carboxy and salts and esters thereof, $(C_{1-6})$alkanoyloxy, arylcarbonyloxy, heterocyclylcarbonyloxy and acyl groups.

Any alkyl group or moiety referred to herein may be straight or branched, unsubstituted or substituted, and may contain, for example, up to 12 carbon atoms, suitably up to 6 carbon atoms. In particular, the alkyl group or moiety may be an unsubstituted or substituted methyl, ethyl, n-propyl, iso-propyl, n-butyl, sec-butyl, isobutyl or tert-butyl group. Examples of suitable optional substitutents for any such alkyl group or moiety include the above-listed substitutents for hydrocarbon groups, and also the above-listed non-alkyl hydrocarbon groups, for example $(C_{2-6})$alkenyl and aryl groups.

The term 'aryl' as used herein includes phenyl and naphthyl, which may be unsubstituted or substituted by up to five, preferably up to three, groups selected from the above-listed substituents for hydrocarbon groups, and the above-listed hydrocarbon groups, including, for example, substituents selected from halogen, $(C_{1-6})$alkyl, phenyl, $(C_{1-6})$alkoxy, halo$(C_{1-6})$alkyl, hydroxy, amino, nitro, carboxy, $(C_{1-6})$alkoxycarbonyl, $(C_{1-6})$alkoxycarbonyl$(C_{1-6})$alkyl, $(C_{1-6})$ alkanoyloxy, and $(C_{1-6})$alkanoyl groups.

The term 'acyl' as used herein includes formyl, unsubstituted and substituted hydrocarbon-carbonyl and hydrocarbonoxy-carbonyl groups, including, for example, unsubstituted and substituted alkanoyl, cycloalkylcarbonyl, arylcarbonyl, alkoxycarbonyl, aryloxycarbonyl, and heterocyclylcarbonyl groups. The term 'acyloxy' is used analogously.

The term 'heterocyclyl' and 'heterocyclic' as used herein include aromatic and non-aromatic, single and fused, rings suitably containing up to four hetero-atoms in each ring selected from oxygen, nitrogen and sulphur, which rings may be unsubstituted or substituted by, for example, up to three groups selected form halogen, $(C_{1-6})$alkyl, $(C_{1-6})$alkoxy, halo$(C_{1-6})$alkyl, hydroxy, amino, carboxy, carboxy salts, carboxy esters, $(C_{1-6})$alkoxycarbonyl, $(C_{1-6})$alkoxycarbonyl$(C_{1-6})$alkyl, aryl, and oxo groups. Each heterocyclic ring suitably has from 4 to 7, preferably 5 or 6, ring atoms. A fused heterocyclic ring system may include carbocyclic rings and need include only one heterocyclic ring.

The term 'heteroaryl' as used herein means an aromatic heterocyclic ring or ring system, suitably having 5 or 6 ring atoms in each ring.

In one group of compounds of the general formula I, $R^1$ and $R^2$ together denote an oxo group, as in naturally occurring erythromycins. In a second group of compounds of the general formula I, $R^1$ and $R^2$ together denote an oxime group (also referred to as a hydroxyimino group, =NOH) or a substituted oxime group (for example, an oxime ether group or an acyl-oxime group). Such compounds may be referred to as erythromycin oxime derivatives. In a third grop of compounds of the general formula I, $R^1$ and $R^2$ together denote an imino group, and such compounds may be referred to as erythromycin imines. In a fourth group of compounds of the general formula I, one of $R^1$ and $R^2$ denotes an amino group or a substituted amino group, and the other of $R^1$ and $R^2$ denotes a hydrogen atom; such compounds may be referred to as erythromycylamines. In a fifth group of compounds of the general formula I, one of $R^1$ and $R^2$ denotes a hydrogen atom and the other of $R^1$ and $R^2$ together with $R^5$ denotes a 9,11-cyclic-(optionally substituted)-methylenedioxy group of the formula (III), as discussed in more detail below; such compounds may be referred to as erythromycin 9,11-acetals or 9,11-ketals.

In the case of the erythromycin oxime and substituted-oxime derivatives according to the invention, $R^1$ and $R^2$ may together denote a group of the formula IV:

$$=N\sim O-R^{11} \qquad \text{IV}$$

in which $R^{11}$ denotes hydrogen or an unsubstituted or substituted hydrocarbon group or an acyl group. Examples of suitable groups denoted by $R^{11}$ include unsubstituted and substituted alkyl, cycloalkyl, alkenyl, and aryl (preferably phenyl) groups, and also unsubstituted and substituted hydrocarbon-carbonyl and hydrocarbonoxy-carbonyl groups, for example unsubstituted and substituted alkanoyl, cycloalkylcarbonyl, arylcarbonyl, alkoxycarbonyl, and aryloxycarbonyl groups; each of the said alkyl groups and moieties suitably having up to 6 carbon atoms.

Examples of suitable substituents for the hydrocarbon group $R^{11}$ include $(C_{1-6})$alkyl, heterocyclyl, amino, $(C_{1-6})$alkanoylamino, (mono, di, or tri)-$(C_{1-6})$-alkylamino, hydroxy, $(C_{1-6})$alkoxy, mercapto, sulphamoyl, carbamoyl, amidino, guanidino, nitro, chloro, bromo, fluoro, carboxy, carboxy salts, carboxy esters, $(C_{1-6})$alkanoyloxy, arylcarbonyl, and heterocyclylcarbonyl groups, and also a group of the formula V:

$$-S(O)_nR^{12} \qquad \text{V}$$

in which n denotes 0, 1 or 2, and $R^{12}$ denotes a $(C_{1-6})$alkyl, heterocyclyl, or aryl group.

Examples of acyl groups $R^{11}$ include acetyl and benzyloxycarbonyl groups.

Examples of unsubstituted alkyl groups $R^{11}$ include methyl, ethyl, n-propyl, isopropyl, n-butyl, sec-butyl, and tert-butyl groups. Examples of substituted alkyl groups $R^{11}$ include aralkyl (especially benzyl), alkoxyalkyl, alkenyloxyalkyl, alkynyloxyalkyl, aryloxyalkyl, aralkoxyalkyl, alkoxyalkoxyalkyl (for example, β-methoxyethoxymethyl), alkylthioalkyl, alkenylthioalkyl, alkynylthioalkyl, arylthioalkyl, aralkylthioalkyl, haloalkyl, formylalkyl, carboxyalkyl and salts and esters thereof, thiocyanatoalkyl, cyanoalkyl, acylalkyl, carbamoylalkyl, and aminoalkyl groups; each of the said alkyl, alkenyl and alkynyl moieties suitably having up to 6 carbon atoms; each of the said thio derivatives optionally being oxidised to the corresponding sulphoxide or sulphone derivative; and the said amino moiety of the said aminoalkyl groups suitably being of the formula VI:

$$\begin{array}{c} R^{13} \\ | \\ -N \\ | \\ R^{14} \end{array} \qquad \text{VI}$$

in which each of $R^{13}$ and $R^{14}$, which may be identical or different, denotes hydrogen or an unsubstituted or substituted hydrocarbon group, advantageously an alkyl group, preferably having from 1 to 6 carbon atoms, or $R^{13}$ and $R^{14}$ and the nitrogen atom to which they are attached together denote an unsubstituted or substituted, unsaturated or saturated heterocyclic ring, optionally containing one or more heteroatoms additional to the said nitrogen atom, each of $R^{13}$ and $R^{14}$ preferably denoting a hydrogen atom.

Erythromycin oximes and substituted-oximes having 9-substituents of the type described above have been described in, for example, GB No. 1 100 504, E. H. Massey et al, G. H. Timms et al, U.S. Pat. No. 3,681,326, 3,869,445, 4,063,014 and 4,349,545, all op. cit.

The erythromycin oxime and substituted oxime derivatives according to the invention can exist in two geometric isomeric forms about the C=N double bond at the 9-position, as indicated by the wavy line in formula IV above, namely the E-form and the Z-form. The E-form is generally preferred.

In the case of the erythromycin imine derivatives according to the invention, $R^1$ and $R^2$ together denote a group of the formula VII:

$$=N-H \qquad \text{VII}$$

Erythromycin imine has been described, for example, in G. H. Timms et al, op. cit.

In the case of the erythromycylamine derivatives according to the invention, one of $R^1$ and $R^2$ denotes hydrogen and the other of $R^1$ and $R^2$ may denote a group of the formula VI above, in which $R^{13}$ and $R^{14}$ are defined as above. Suitably each of $R^{13}$ and $R^{14}$ denotes a hydrogen atom or an alkyl group having up to 6 carbon atoms. Erythromycylamine and derivatives thereof have, for example, been described in GB No. 1 100 504, E. H. Massey et al and G. H. Timms et al, all op. cit.

The erythromycylamine derivatives according to the invention can exist in two isomeric forms at the 9-position, namely the (9R)-form, in which $R^1$ denotes hydrogen and $R^2$ denotes the optionally substituted amino group, and the (9S)-form, in which $R^1$ denotes the optionally substituted amino group and $R^2$ denotes hydrogen. The (9S)-isomer is preferred.

The erythromycin derivatives according to the invention are characterised by a 6-carbamate group, —OCONH$_2$, which may optionally be N-substituted. In particular, the carbamate group may be N-substituted by an acyl group, for example a hydrocarbylcarbonyl group, or a hydrocarbylsulphonyl group. Examples of N-substituted-carbamate groups include those of the formula VIII:

$$-O-CO-NH-X-R^{15} \qquad \text{VIII}$$

in which

X denotes —CO— or —SO$_2$—, and $R^{15}$ denotes an unsubstituted or substituted hydrocarbon group, such as the residue of an organic carboxylic or sulphonic acid.

Examples of suitable groups $R^{15}$ include unsubstituted or substituted $(C_{1-6})$alkyl and aryl groups, for example halo$(C_{1-6})$alkyl, $(C_{1-6})$alkoxy$(C_{1-6})$alkyl, phenyl, $(C_{1-6})$alkylphenyl, and halophenyl groups, especially methyl, halomethyl (e.g. trichloromethyl), methoxymethyl, phenyl, tolyl, and halophenyl groups.

In the compounds of the general formula I, the 12-substituent denoted by $R^4$ is preferably a hydroxy group as in the erythronolide A ring, or, in other words, the compounds of the general formula I are preferably derivatives of erythromycin A. Alternatively, the present compounds may be derivatives of erythromycin B, in which case $R^4$ denotes a hydrogen atom, or of another naturally occurring erythromycin.

The 11-position o the erythronolide ring may carry a hydroxy group or an etherified hydroxy group. The etherified hydroxy group $R^5$ may be an alkoxy group or a group of the formula IX or X:

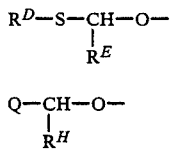

$$R^D\text{—S—CH—O—} \quad \text{IX}$$
$$\quad \quad |$$
$$\quad \quad R^E$$

$$Q\text{—CH—O—} \quad \text{X}$$
$$\quad |$$
$$\quad R^H$$

in which formulae

Q denotes one of the following groups:

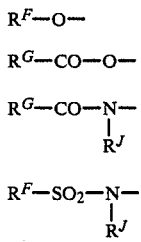

$$R^F\text{—O—} \quad \text{XIA}$$

$$R^G\text{—CO—O—} \quad \text{XIB}$$

$$R^G\text{—CO—N—} \quad \text{XIC}$$
$$\quad \quad \quad |$$
$$\quad \quad \quad R^J$$

$$R^F\text{—SO}_2\text{—N—} \quad \text{XID}$$
$$\quad \quad \quad |$$
$$\quad \quad \quad R^J$$

$R^D$ denotes an alkyl group, $R^E$ denotes hydrogen or an alkyl group, $R^F$ denotes an unsubstituted or substituted hydrocarbon group, $R^G$ denotes a hydrogen atom or an unsubstituted or substituted hydrocarbon or hydrocarbonoxy group, each of $R^H$ and $R^J$, which may be identical or different, denotes a hydrogen atom or an unsubstituted or substituted hydrocarbon group, or any two of $R^F$, $R^G$, $R^H$ and $R^J$ together denote a divalent, unsubstituted or substituted, organic group forming a 4- to 7-membered heterocyclic ring together with the intervening atoms of the molecule.

Suitably, the 11-position carries a hydroxy group, as in naturally-occuring erythromycins, in which case $R^5$ denotes hydroxy.

In the event that the 11-position carries an etherified hydroxy group, $R^5$ suitably denotes an alkoxy group, advantageously a ($C_{1-6}$)alkoxy group, preferably a methoxy group. 11-O-Alkyl-erythromycin derivatives have been described in U.S. Pat. No. 3,884,904, EP No. 0 041 355 A1, EP No. 0 080 818 A1, and EP No. 0 080 819 A1, all op. cit.

In the event that $R^5$ denotes a group of the formula IX above, $R^E$ suitably denotes a hydrogen atom or a ($C_{1-6}$)alkyl group and $R^D$ suitably denotes a ($C_{1-6}$)alkyl group, preferably a methyl group. An example of a group $R^5$ of the formula IX is a methylthiomethoxy group. 11-O-Alkylthioalkylerythromycin derivatives have been described in U.S. Pat. Nos. 3,842,069 and 3,884,904, both op. cit.

Further suitable etherified hydroxy groups $R^5$ include hydrocarbonoxymethoxy, acyloxymethoxy (including formyloxymethoxy), acylaminomethoxy (including formylaminomethoxy), and sulphonamidomethoxy groups of the formula X defined above, especially those of the formula X in which Q denotes a group of the formula XIA.

In the etherified hydroxy groups of the formula X, suitably, $R^F$ denotes an unsubstituted or substituted alkyl, alkenyl, aryl, or cycloalkyl group. Suitably, $R^G$ denotes a hydrogen atom or an unsubstituted or substituted alkyl, alkoxy, aryl, aryloxy, cycloalkyl, or cycloalkyloxy group. Suitably, the alkyl group $R^F$ or $R^G$ is a ($C_{1-6}$)alkyl group, for example a methyl, ethyl, propyl or butyl group, especially a methyl or ethyl group. Suitably, the aryl group $R^F$ or $R^G$ may be a phenyl group, and the aryloxy group $R^G$ may be a phenoxy group. The cycloalkyl group or moiety suitably has from 3 to 7 carbon atoms, for example a cyclohexyl group or moiety.

Examples of substituents for substituted hydrocarbon groups $R^F$ or $R^G$ and for substituted hydrocarbonoxy groups $R^G$ include hydroxy, halogen, carboxy, alkoxy, aryloxy, formyl, acyloxy (for example, alkanoyloxy and arylcarbonyloxy, especially formyloxy and benzoyloxy), alkoxycarbonyl, hydrocarbon-sulphonyloxy (for example, alkanesulphonyloxy), substituted-silyloxy (for example trialkylsilyloxy), amino (which may suitably be of the formula VI above, for example N-alkylamino and N,N-dialkylamino), oxo, azido, diazo, and heterocyclyl (especially nitrogen-containing heterocyclyl bonded through a ring-nitrogen atom, for example triazolyl, piperidinyl, and phthalimido, and also heteroaryl) groups.

Suitably, $R^H$ denotes a hydrogen atom. Suitably, $R^J$ denotes an alkyl group (especially amethyl group) or a hydrogen atom. In the event that $R^H$ and/or $R^J$ denotes an unsubstituted or substituted hydrocarbon group, it may advantageously be an unsubstituted or substituted alkyl, cycloalkyl or aryl group. Suitably, the alkyl group is a ($C_{1-6}$)alkyl group, for example a methyl or ethyl group. Suitably, the aryl group may be a phenyl group. The cycloalkyl group suitably has from 3 to 7 carbon atoms, for example the cyclohexyl group. An example of a substituted alkyl group is an aralkyl group, for example a benzyl group. Suitably $R^H$ and/or $R^J$ denotes an alkyl group.

In the event that two of $R^F$, $R^G$, $R^H$ and $R^J$ together denote a divalent, unsubstituted or substituted, organic group completing a 4- to 7-membered heterocyclic ring, the said ring may be saturated or unsaturated and may optionally contain hetero-atoms additional to those shown in the respective formula. Such additional hetero-atoms suitably include oxygen, sulphur, and nitrogen atoms. Suitably, two of $R^F$, $R^G$, $R^H$ and $R^J$ together denote an alkylene group, for example an ethylene, propylene or butylene group. For example, the group of the formula X may be a tetrahydrofuryloxy or pyrrolid-2-on-1-ylmethoxy group.

Further examples of suitable substitutents for a hydrocarbon group $R^F$ to $R^J$, a hydrocarbon-oxy group $R^G$, and a divalent organic group denoted by two of $R^F$, $R^G$, $R^H$ and $R^J$ include, in particular, alkoxy, alkoxyalkoxy, aryloxy, hydroxy, amino, substituted amino (for example, monoalkylamino and dialkylamino), carboxy, esterified carboxy (for example, alkoxycarbonyl), acyloxy (for example, alkanoyloxy), carbamoyl ($H_2N$—C(=O)—), and substituted carbamoyl (for example, N-alkylcarbamoyl and N,N-dialkylcarbamoyl) groups. Any aryl or alkyl moiety in such substituents may itself be substituted by, for example, an alkyl or aryl group or one of the listed substituents, and any alkyl moiety advantageously contains not more than 6, preferably not more than 4, carbon atoms. An example of a substituent in which an alkyl moiety is itself substituted is an alkoxyalkoxy substituent.

Particularly preferred groups of the formula X are those in which Q denotes a group of the formula XIA especially those in which $R^F$ denotes a 2-substituted-ethyl or 3-substituted propyl group, wherein the substituent may, for example, be one of the substituents listed above as a suitable substituent for the group $R^F$, including, for example, amino, N-alkylamino, N,N-dialkylamino, halogen, hydroxy, alkoxy, benzoyloxy, alkanesulphonyloxy, trisilyloxy, alkoxycarbonyl, alkanoyloxy, phenoxy, and heterocyclyl groups.

Erythromycin 11-ethers containing an etherified hydroxy group of the formula X are described and claimed in our European Patent Application No. 86301685.3 filed 10 March 1986 and corresponding foreign applications based on British Patent Applications Nos. 85.06381, 85.07626 and 86.00553, filed Mar. 12, 1985, Mar. 23, 1985 and Jan. 10, 1986, respectively.

Alternatively, the compounds of the general formula I may contain, in place of the 11- and 12-substituents discussed above, an 11,12-cyclic carbonate group, in which case $R^4$ and $R^5$ together denote a cyclic carbonate group of the formula II above. 11,12-cyclic carbonate derivatives of erythromycin have been described by T. Glabski et al, op. cit.

Moreover, as a further option, the compounds of the general formula I may contain a 9,11- or 11,12-cyclic-(optionally substituted)methylenedioxy group, in which case $R^5$, together with $R^1$ or $R^2$ or $R^4$, denotes a group of the formula III above. In formula III, $R^A$ and $R^B$ may be identical or different and each denotes a hydrogen atom or a hydrocarbon group.

The hydrocarbon group $R^A$, $R^B$ may suitably be an unsubstituted or substituted alkyl group, more particularly a lower alkyl group, preferably a $(C_{1-6})$alkyl group, for example a methyl or ethyl group, or may be an unsubstituted aryl group, for example a phenyl group. Suitably, at least one of $R^A$ and $R^B$ denotes a hydrogen atom. Advantageously, both of $R^A$ and $R^B$ denote hydrogen atoms. In another embodiment, both of $R^A$ and $R^B$ denote alkyl groups. In another embodiment, one of $R^A$ and $R^B$ denotes a hydrogen atom and the other of $R^A$ and $R^B$ denotes a hydrogen atom or an unsubstituted or substituted alkyl or aryl group. In the case of 9,11-derivatives, $R^A$ and $R^B$ may together denote an unsubstituted or substituted aliphatic carbocyclic group (for example, cyclohexyl).

9,11-O-(optionally substituted)-methylene derivatives of erythromycin are further described and are claimed in our European Patent Application, Publication No. EP No. 0 184 921 A2.

11,12-O-(optionally substituted)-methylene derivatives of erythromycin are further described and are claimed in our International Patent Application, Publication No. WO 86/01513.

The 8-position of the erythronolide ring preferably has only a methyl substituent, as in naturally-occuring erythromycins, and therefore preferably $R^6$ denotes a hydrogen atom. 8-Hydroxy and 8-fluoro derivatives have been described (K. Krowicki et al, L. Toscano et al, and EP No. 0 158 102 A, all op cit.) and $R^6$ may denote a hydroxy group or a fluorine atom.

The —$OR^7$ group in the 3"-position of the cladinose ring may be a hydroxy group or a methoxy group. Preferably, $R^7$ denotes a methyl group as in erythromycin A and B.

The 4"-position of the cladinose ring may suitably carry a hydroxy group as in erythromycin A and B ($R^8$=H; $R^9$=OH). Various modifications of the 4"-position of the cladinose ring have previously been described and those modifications may be incorporated in the compounds according to the present invention:

(i) 4"-deoxy-4"-oxo derivatives ($R^8$+$R^9$=O=) are described in U.S. Pat. Nos. 3,842,069, 3,884,903 and 4,150,220, all op. cit.;

(ii) 4"-epi-hydroxy derivatives ($R^8$=OH; $R^9$=H) and 4"-deoxy-4"-alkanoyloxy-4"-epi derivatives ($R^8$=alkanoyloxy, especially $CH_3COO$-; $R^9$=H) are described in U.S. Pat. Nos. 3,884,903 and 4,382,085, both op. cit.;

(iii) 4"-O-alkyl derivatives ($R^8$ or $R^9$=alkoxy, especially methoxy; the other of $R^8$ and $R^9$=H) are described in EP No. 0 080 818 Al, op. cit.;

(iv) 4"-deoxy-4"-amino derivatives ($R^8$ or $R^9$=amino or substituted amino; the other of $R^8$ and $R^9$=H) are described in U.S. Pat. No. 4,150,220, op. cit.;

(v) 4"-deoxy-4"-oxime derivatives ($R^8$+$R^9$=oxime (=N—OH) or substituted oxime, especially acetyloxime (=N—O—CO—$CH_3$)) are also described in U.S. Pat. No. 4,150,220, op cit.;

(vi) 4"-O-sulphonyl derivatives ($R^8$=H, $R^9$=Rc—$SO_2$-O-) are described in U.S. Pat. No. 3,836,519, 3,869,445 and 4,063,014, all op cit.; and (vii) 4"-deoxy derivatives ($R^8$=$R^9$=H) are described in JP No. 58-049396, op cit.

In the 4"-deoxy-4"-(substituted amino) derivatives, the substituted amino group $R^8$ or $R^9$ may suitably be a group of the formula XII or XIII:

—$NHCOR^{16}$      XII or

—$NHSO_2R^{16}$      XIII in which $R^{16}$ denotes a hydrocarbon group.

In the 4"-O-sulphonyl derivatives, in which $R^8$ or $R^9$ denotes a sulphonyloxy group of the formula XIV:

$R^C$—$SO_2$—O—,      XIV the organic group $R^C$ may suitably be an unsubstituted or substituted hydrocarbon, oxahydrocarbon, thiahydrocarbon or azahydrocarbon group, more especially an alkyl, alkenyl, unsubstituted or substituted aryl (especially phenyl, nitrophenyl, halophenyl or alkylphenyl), unsubstituted or substituted aralkyl (especially benzyl, nitrobenzyl, halobenzyl or alkylbenzyl), unsubstituted or substituted aryloxyalkyl (especially phenoxyalkyl, nitrophenoxyalkyl, halophenoxyalkyl or alkylphenoxyalkyl), or substituted ethyl (especially $R^{17}$—$CH_2$—$CH_2$—, wherein $R^{17}$ is defined as below) group.

Examples of groups $R^{17}$ in the 4"-substituent $R^{17}$—$CH_2$—$CH_2$—$SO_2$—O—      XV include amino, substituted amino, carbamoyl, substituted carbamoyl, sulphamoyl, substituted sulphamoyl, substituted ureido, substituted thioureido, alkoxy, alkythio, optionally substituted aryloxy, optionally substituted arylthio, optionally substituted benzyloxy, optionally substituted benzylthio, substituted suphonyl, substituted sulphinyl, substituted alkyl, substituted alkanoyl, substituted cyano, and other groups more specifically described in U.S. Pat. Nos. 3,869,445 and 4,063,014, op. cit.

Preferably, $R^C$ denotes a hydrocarbon group, particularly a $(C_{1-6})$alkyl group, especially a methyl group.

The present invention includes pharmaceutically acceptable esters, especially in vivo hydrolysable esters, of the compounds of the general formula I. Such esters may be formed at any hydroxy group in the compounds of the general formula I, but usually the ester will be formed at the 2′-hydroxy group of the desosamine ring, thus giving a 2′-O-acyl derivative of the type described in U.S. Pat. No. 2,862,921 (R. E. Booth et al; Upjohn Co.), U.S. Pat. No. 2,993,833 (V. C. Stephens; Eli Lilly), U.S. Pat. Nos. 3,836,519, 3,842,069, 3,869,445, 3,884,903, 3,884,904 and 4,150,220, all op. cit.

Suitable pharmaceutically acceptable in vivo hydrolysable esters include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic, and alkanedioic acids, in which each alkyl or alkenyl moiety advantageously has not more than 6 carbon atoms. Examples of particular esters include formates, acetates, propionates, butyrates, acrylates, and ethylsuccinates.

Moreover, the ester derivatives of the compounds of the general formula I include (optionally substituted)-carbamoyl esters, for example those in which the ester group is of the formula $-OCONH_2$ or of the formula VIII above. Such carbamates may be formed at any hydroxy group in the compounds of the general formula I, including, in particular, the 11-, 12-, 2′- and 4″-hydroxy groups, and also any other hydroxy groups that may be present, such as at the 8- and 3″-positions or in substituents at the 11- and 4″-positions.

The present invention also includes acid addition salts, especially pharmaceutically acceptable acid addition salts, of the compounds of the general formula I. Such acid addition salts may, in particular, be formed at the 3′-dimethylamino group of the desosamine ring.

Various acid addition salts of erythromycin are described in U.S. Pat. No. 2,761,859 (C. E. Hoffhine, Jr.; Abbott Laboratories) and U.S. Pat. No. 2,852,429 (J. T. Shepler; Eli Lilly).

Suitable acid addition salts of the compounds of the invention include pharmaceutically acceptable inorganic acid addition salts, for example the sulphate, nitrate, phosphate, borate, hydrochloride and hydrobromide, and also pharmaceutically acceptable organic acid addition salts, for example the acetate, tartrate, maleate, citrate, succinate, benzoate, ascorbate, methane-sulphate, α-keto-glutarate, α-glycerophosphate, and glucose-1-phosphate. Preferably the acid addition salt is the laurylsulphate salt.

Examples of individual compounds according to the present invention include:

(i) erythromycin A 6-carbamate 9-oxime (in general formula I, $R^1+R^2===N-OH$; $R^3=CONH_2$; $R^4=R^5=OH$; $R^6=H$; $R^7=CH_3$; $R^8=H$; $R^9=OH$);

(ii) erythromycin A 6-carbamate 9-oxime 11,12-carbonate (in general formula I, $R^4+R^5=-OC(O)O-$; $R^1+R^2$, $R^3$ and $R^6$ to $R^9$ as for compound (i));

(iii) erythromycin A 6-carbamate (in general formula I, $R^1+R^2===O$; $R^3$ to $R^9$ as for compound (i));

(iv) erythromycin A 6,11-dicarbamate 9-methoxime (in general formula I, $R^1+R^2===N-OCH_3$; $R^5=OCONH_2$; $R^3$, $R^4$ and $R^6$ to $R^9$ as for compound (i));

(v) erythromycin A 6-carbamate 9-methoxime 11,12-carbonate (in general formula I, $R^1+R^2===N-OCH_3$; $R^3$ to $R^9$ as for compound (ii));

(vi) erythromycin A 6-carbamate 9-imine (in general formula I, $R^1+R^2===NH$; $R^3$ to $R^9$ as for compound (i));

(vii) erythromycylamine 6-carbamate (in general formula I, $R^1$, $R^2=-NH_2$, $-H$; $R^3$ to $R^9$ as for compound (i));

(viii) erythromycin A 6-carbamate 11,12-carbonate (in general formula I, $R^1+R^2===O$; $R^3$ to $R^9$ as for compound (ii));

(ix) erythromycin A 6-carbamate 9-methoxime (in general formula I, $R^1+R^2===N-OCH_3$; $R^3$ to $R^9$ as for compound (i));

(x) erythromycin A 6,12-dicarbamate 9-methoxime 11-formate (in general formula I, $R^1+R^2===N-OCH_3$; $R^3=CONH_2$; $R^4=OCONH_2$; $R^5=OCHO$; $R^6$ to $R^9$ as for compound (i));

(xi) erythromycin A 6-carbamate 9-(2-methoxyethoxymethoxime) (in general formula I, $R^1+R^2===N-OCH_2OCH_2CH_2OCH_3$; $R^3$ to $R^9$ as for compound (i));

(xii) erythromycin A 6-benzoylcarbamate 9-oxime (in general formula I, $R^3=-OCONHCOC_6H_5$; $R^1+R^2$ and $R^4$ to $R^9$ as for compound (i));

(xiii) erythromycin A 6-benzoylcarbamate 9-oxime 11,12-carbonate (in general formula I, $R^3$ as for compound (xii); $R^1+R^2$ and $R^4$ to $R^9$ as for compound (ii));

(xiv) erythromycin A 6-benzoylcarbamate 9-methoxime 11,12-carbonate (in general formula I, $R^1+R^2===N-OCH_3$; $R^3$ to $R^9$ as for compound (xiii));

(xv) erythromycin A 6-benzoylcarbamate 9-methoxime (in general formula I, $R^1+R^2===N-OCH_3$; $R^3$ to $R^9$ as for compound (xii));

(xvi) erythromycin A 6,12-bis-acetylcarbamate 9-methoxime 11-formate (in general formula I, $R^3=-CONHCOCH_3$; $R^4=-OCONHCOCH_3$; $R^1+R^2$ and $R^5$ to $R^9$ as for compound (x));

(xvii) erythromycin A 6-acetylcarbamate 9-methoxime 11,12-carbonate (in general formula I, $R^3=-CONHCOCH_3$; $R^1+R^2$ and $R^4$ to $R^9$ as for compound (xiv));

(xviii) 9-dihydro-9,11-ethylidene-erythromycin A 6-carbamate (in general formula I, one of $R^1$ and $R^2=H$; the other of $R^1$ and $R^2=H$; the other of $R^1$ and $R^2+R^5=-O-CH(CH_3)-O-$; $R^3$, $R^4$ and $R^6$ to $R^9$ as for compound (i));

(xix) erythromycin A 6-methoxyacetylcarbamate 9-methoxime 11,4″-diformate (in general formula I, $R^1+R^2===N-OCH_3$; $R^3=-CONHCOCH_2OCH_3$; $R^4=OH$; $R^5=-OCHO$; $R^6=H$; $R^7=CH_3$; $R^8$, $R^9=-H$, $-OCHO$);

(xx) erythromycin A 6,12-methoxyacetylcarbamate 9-methoxime 11,4″-diformate (in general formula I, $R^4=-OCONHCOCH_2OCH_3$; $R^1+R^2$, $R^3$ and $R^5$ to $R^9$ as for compound (xix));

(xxi) erythromycin A 6-p-toluenesulphonylcarbamate 9-methoxime 11,4″-diformate (in general formula I, $R^3=-CONH-SO_2-C_6H_4-p-CH_3$; $R^1+R^2$ and $R^4$ to $R^9$ as for compound (xix));

(xxii) erythromycin A 6,12-bis-p-toluenesulphonylcarbamate 9-methoxime 11,4″-diformate (in general formula I, $R^4=-OCONH-SO_2-C_6H_4-p-CH_3$; $R^1+R^2$, $R^3$ and $R^5$ to $R^9$ as for compound (xxi));

(xxiii) 11-O-(2-hydroxyethoxymethyl)-erythromycin A 6-carbamate 9-oxime (in general formula I, $R^5=-OCH_2OCH_2CH_2OH$, $R^1+R^2$, $R^3$, $R^4$ and $R^6$ to $R^9$ as for compound (i));

(xxiv) 11-O-(2-hydroxyethoxymethyl)-erythromycin A 6,12-dicarbamate 9-oxime (in general formula I, $R^4$=—OCONH$_2$; $R^1+R^2$, $R^3$ and $R^4$ to $R^9$ as for compound (xxiii));

(xxv) 11-O-(2-N,N-dimethylaminoethoxymethyl)erythromycin A 6-carbamate 9-oxime (in general formula I, $R^5$=—OCH$_2$OCH$_2$CH$_2$N(CH$_3$)$_2$; $R^1+R^2$, $R^3$, $R^4$ and $R^6$ to $R^9$ as for compound (i));

(xxvi) 11-O-(2-N,N-dimethylaminoethoxymethyl)erythromycin A 6-carbamate (in general formula I, $R^1+R^2$==O; $R^3$ to $R^9$ as for compound (xxv));

(xxvii) 11-O-ethoxymethyl-erythromycin A 6-carbamate 9-oxime (in general formula I, $R^5$=—OCH$_2$OCH$_2$CH$_3$; $R^1+R^2$, $R^3$, $R^4$ and $R^6$ to $R^9$ as for compound (i));

(xxviii) 11-O-ethoxymethyl-erythromycin A 6,12-dicarbamate 9-oxime (in general formula I, $R^4$=—OCONH$_2$; $R^1+R^2$, $R^3$ and $R^5$ to $R^9$ as for compound (xxvii));

(xxix) 11-O-ethoxymethyl-erythromycin A 6-carbamate 9-methoxime (in general formula I, $R^1+R^2$==N—OCH$_3$; $R^3$ to $R^9$ as for compound (xxvii)); and (xxx) erythromycin A 6-p-toluenesulphonylcarbamate 9-methoxime (in general formula I, $R^1+R^2$==N—OCH$_3$; $R^3$=—CONH—SO$_2$—C$_6$H$_4$—p—CH$_3$; $R^4$ to $R^9$ as for compound (i));

as well as corresponding 11-ether, 9,11-O-methylene and 11,12-O-methylene derivatives, and corresponding derivatives in which the 8-position and/or the 4"-position is modified as discussed above;

and also pharmaceutically acceptable esters and acid addition salts of such compounds.

The 6-carbamate erythromycin derivatives according to the invention may be prepared by reacting an erythromycin or erythromycin 9-oxime, 9-substituted-oxime or 9,11-ketal or -acetal derivative having a hydroxy substituent at the 6-position, in which any reactive groups (other than the 6-hydroxy group) may optionally be protected, with a reagent capable of introducing a carbamoyl group; and thereafter if necessary carrying out one or more of the following steps:

(a) converting a substituent on the erythromycin structure to another such substituent in a conventional manner;

(b) removing any protecting groups; and (c) forming a pharmaceutically acceptable ester or acid addition salt.

A resulting 9-oxo compound according to the invention may, if desired, optionally be converted to a 9-oxime or 9-substituted-oxime compound according to the invention or to a 9,11-acetal or -ketal compound according to the invention.

A suitable resulting 9-substituted-oxime (for example a 9-acyloxime) compound according to the invention may, if desired, subsequently be converted to a 9-oxo or 9-oxime compound according to the invention. A resulting 9-oxime compound according to the invention may, if desired, be converted to a 9-substituted-oxime, 9-oxo, or 9-imino compound according to the invention.

A resulting 9-imino compound may, in turn, be converted to a 9-oxo or 9-amino compound according to the invention, which latter compound may, if desired, be further converted to a 9-substituted amino compound according to the invention.

More particularly, a compound of the general formula I as hereinbefore defined or a pharmaceutically acceptable ester or acid addition salt thereof may be prepared by a process which comprises reacting a compound of the general formula XVI:

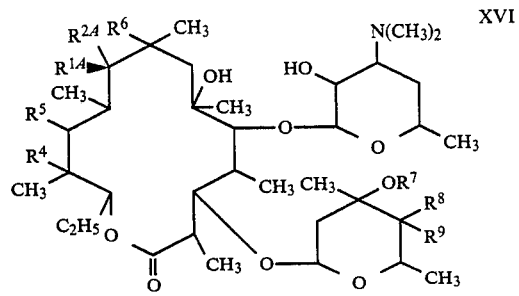

wherein $R^4$, $R^5$, $R^6$, $R^7$, $R^8$ and $R^9$ are defined as above with respect to general formula I, and $R^{14}$ and $R^{24}$ together denote an oxo, oxime or substituted oxime group, or one of $R^{14}$ and $R^{24}$ denotes a hydrogen atom, and the other of $R^{14}$ and $R^{24}$ together with $R^5$ denotes a group of the formula III above, in which compound of the general formula XVI any reactive group (other than the 6-hydroxy group) may optionally be protected, with an organic acid isocyanate, to give a compound of the general formula I in which $R^1$ and $R^2$ together denote an oxo, oxime or substituted oxime group, or in which one of $R^1$ and $R^2$ denotes a hydrogen atom and the other of $R^1$ and $R^2$ together with $R^5$ denotes a group of the formula III above; and thereafter, if necessary or desired, carrying out one or more of the following steps in any suitable order:

(a) converting an oxo group denoted by $R^1$ and $R^2$ together to an oxime group or a substituted oxime group, or, jointly with a hydroxy group denoted by $R^5$, to a group of the formula III denoted by $R^5$ together with $R^1$ or $R^2$, the other of $R^1$ and $R^2$ denoting a hydrogen atom;

(b) converting a substituted oxime group denoted by $R^1$ and $R^2$ together to another substituted oxime group, an oxime group, or an oxo group;

(c) converting an oxime group denoted by $R^1$ and $R^2$ together to a substituted oxime group, an oxo group, or an imino group;

(d) converting a resulting imino group denoted by $R^1$ and $R^2$ together to an oxo group or to an amino group denoted by $R^1$ or $R^2$;

(e) converting a resulting amino group denoted by $R^1$ or $R^2$ to a substituted amino group;

(f) converting any one or more of the groups denoted by $R^5$, $R^6$, $R^8$ and $R^9$ to another such group;

(g) removing any protecting group that may be present; and (h) forming a pharmaceutically acceptable ester or acid addition salt.

The compound of the general formula XVI in which:
each of $R^4$, $R^5$ and $R^9$ denotes hydroxy,
each of $R^6$ and $R^8$ denotes hydrogen, and
$R^7$ denotes methyl,
is erythromycin A or a 9-oxime or a 9-substituted-oxime derivative thereof. The 9-oxime and 9-substituted-oxime derivatives may be prepared from erythromycin A by known methods, for example by the methods described in the above-cited references relating to erythromycin 9-oximes and 9-substituted-oximes.

The compound of the general formula XVI in which:
each of $R^4$, $R^6$ and $R^8$ denotes hydrogen,
each of $R^5$ and $R^9$ denotes hydroxy, and
$R^7$ denotes methyl, is erythromycin B or a 9-oxime or a 9-substituted-oxime derivative thereof. The 9-oxime and 9-substituted-oxime derivative may be prepared from erythromycin B by analogous known methods.

Compounds of the general formula XVI in which $R^5$ denotes an alkoxy group or an etherified hydroxy group of the formula IX above may be prepared by the methods described in the respective references cited above.

Compounds of the general formula XVI in which $R^5$ denotes an etherified hydroxy group of the formula X above may be prepared by the method described in our European Patent Application No. 86301685.3 cited above. In that method, erythromycin or an erythromycin derivative (in particular, an erythromycin 9-oxime or 9-substituted-oxime) having a hydroxy substituent at the 11-position, and suitably having other reactive groups (including, in particular, the 3'-dimethylamino group) protected as hereinafter described, is reacted with an alkylating agent of the general formula XVII:

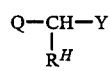  XVII in which
Q and $R^H$ are defined as above, and
Y denotes a leaving group, for example an alkylsulphonyloxy or arylsulphonyloxy group (e.g. methanesulphonyloxy or p-toluenesulphonyloxy) or, preferably, a halogen atom, especially a chlorine atom.

The alkylation is conveniently carried out under weakly basic conditions, suitably using a weak non-nucleophilic organic base (preferably a tertiary amine, for example a substituted pyridine, e.g. a lutidine or collidine), in an inert organic solvent (for example N,N-dimethyl-formamide, dimethylsulphoxide, tetrahydrofuran, or dichloromethane), preferably at about ambient temperature, such as 15° to 30° C. The alkylating agent is conveniently used in an amount of from 1 to 5 moles per mole of the erythromycin compound, and the base is conveniently used in a molar excess with respect to the alkylating agent (for example, an excess of from 1.5:1 to 2:1). Reactive groups in the alkylating agent may be protected in conventional manner.

Compounds of the general formula XVI in which $R^4$ and $R^5$ together denote an 11,12-cyclic-(optionally substituted)methylenedioxy group of the formula III above may be prepared by the method described in our International Patent Application, Publication No. WO 86/01513, cited above. In that method, erythromycin or an erythromycin derivative (in particular, an erythromycin 9-oxime or 9-substituted-oxime) having a hydroxy substituent at each of the 11- and 12-positions, and suitably having other reactive groups (including, in particular, the 3'-dimethylamino group) protected as hereinafter described, is reacted with:

(i) a compound of the general formula XVIII:

  XVIII or a reactive derivative thereof, for example an acetal, hemiacetal or enol ether of the general formula XVIIIA, XVIIIB or XVIIIC, respectively:

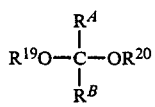  XVIIIA

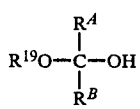  XVIIIB

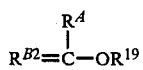  XVIIIC or
(ii) a compound of the general formula XIX:

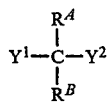  XIX in which formulae
$R^A$ and $R^B$ are defined as above,
$R^{B2}$ denotes a divalent hydrocarbon group corresponding to the monovalent hydrocarbon group $R^B$ with the loss of a hydrogen atom on the carbon atom carrying the free valency,
each of $R^{19}$ and $R^{20}$, which may be identical or different, denotes a hydrocarbon group, advantageously a $(C_{1-6})$ hydrocarbon group, preferably an alkyl group, especially a methyl or ethyl group, and
each of $Y^1$ and $Y^2$, which may be identical or different, denotes a readily displaceable group, for example the groups mentioned above as examples for the group Y, with $Y^1$ and $Y^2$ preferably being different halogen atoms, especially chlorine and iodine respectively.

The reaction according to method (i) is suitably carried out in the presence of an acid catalyst (for example, pyridinium p-toluene-sulphonate or pyridinium chloride), advantageously in the presence of a drying agent (for example, magnesium sulphate or molecular sieves), in an inert solvent (for example, an ether solvent, e.g. tetrahydrofuran; a halogenated solvent, e.g. chloroform; or an aromatic solvent, e.g. toluene), preferably at ambient temperature, such as 10° to 25° C. The reaction according to method (ii) is suitably carried out under strongly basic conditions (suitable bases being, for example, sodium hydride, lithium amide, and potassium t-butoxide), in an inert solvent, suitably a polar aprotic solvent (for example, N,N-dimethylformamide, dimethylsulphoxide, and N-methylpyrrolidone) optionally in conjunction with an ether solvent, preferably at a cool temperature, such as 0° to 15° C.

Compounds of the general formula XVI in which $R^{14}$ or $R^{24}$ together with $R^5$ denotes a 9,11-cyclic-(optionally substituted)methylenedioxy group of the formula III above may be prepared by a method analogous to that used for the corresponding 11,12-derivatives, as described in our European Patent Application, Publication No. EP 0 184 921 A2. In that method, a 9-dihydroerythromycin, having a hydroxy substituent at each of the 9- and 11-positions, and prepared by known methods (for example, as described by P. F. Wiley et al, M. V. Sigal et al, or T. Glabski et al, all op. cit.), and having other reactive groups protected, is reacted according to method (i) or (ii) above.

Other compounds of the general formula XVI may also be prepared, by methods known per se, from erythromycin A or B or the corresponding 9-oxime or 9-substituted-oxime derivative. For example, a compound in which the 8-position or the 4''-position is substituted other than as in naturally-occuring erythromycin A or B (that is to say, in which $R^6$ is fluorine or hydroxy or in which $R^8$ is other than hydrogen and/or $R^9$ is other than hydroxy) may be prepared as described in the respective references cited above.

In general, in the preparation of 9-oxime and 9-substituted-oxime compounds of the general formula XVI, the conversion of the 9-oxo group of erythromycin A or B to a 9-oxime or 9-substituted-oxime group may be effected prior to or subsequent to modification of other positions of the erythromycin molecule.

Prior to carrying out the reaction of a compound of the general formula XVI with an isocyanate, any reactive group of a compound of the general formula XVI (other than the 6-hydroxy group) may optionally be protected.

In particular, the 4''-hydroxy group will generally be protected by acylation in known manner, for example by the method described in Jones et al, *J. Med. Chem.*, 1972, 15, 631. A preferred acyl group for this purpose is the formyl group, which can subsequently readily be removed by hydrolysis.

The 11- and 2'-hydroxy groups may, if desired, conveniently also be protected by acylation simultaneously with the protection of the 4''-hydroxy group. In some cases, however, it may be convenient to protect the 2'-hydroxy group simultaneously with protection of the 3'-dimethylamino group discussed below, suitably using a benzyloxycarbonyl group.

Protection of the 3'-dimethylamino group will often not be necessary when carrying out the process according to the invention. In some cases, however, such protection may be advantageous, particularly when it is intended to carry out additional reactions on the erythromycin molecule such as derivatisations at positions other than the 6-position. Such protection may conveniently be effected by means of an N-protecting group in known manner, for example by the method described by E. H. Flynn et al, (*J. Amer. Chem. Soc.*, 1955, 77, 3104-3106).

Examples of suitable N-protecting groups include benzyloxycarbonyl, and substituted benzyloxycarbonyl, (for example, p-methylbenzyloxycarbonyl, p-nitrobenzyloxycarbonyl, p-bromobenzyloxycarbonyl, p-phenylazobenzyloxycarbonyl, and p-(p'-methoxyphenylazo)-benzyloxycarbonyl). A preferred N-protecting group is benzyloxycarbonyl.

In the event that an erythromycin 9-oxime compound according to the invention is desired, it may in some cases be advantageous to use an erythromycin 9-substituted-oxime compound of the general formula XVI in which the oxime substituent is a protecting group which can readily be removed after completion of the reaction with the isocyanate. Suitable oxime-protecting groups are known in the art and include, for example, the N-protecting groups listed above. If the 3'-dimethylamino group is being protected, it may be convenient to protect the oxime group simultaneously therewith, suitably using a benzyloxycarbonyl group. Protection of a 9-oxime group is not always necessary, however, since it has been found that even though a carbamoyl group may be introduced onto the 9-oxime group during the process according to the invention, it often becomes removed therefrom during subsequent work-up.

Any reactive substituents that may be present in the group $R^8$ or $R^9$ should preferably also be protected in a conventional manner.

In the process according to the invention, the erythromycin compound of the general formula XVI, optionally containing protective groups, is reacted with a reagent capable of introducing a carbamoyl group, that is to say, a reagent that will react with the 6-hydroxy group to form a 6-carbamoyloxy group —$OR^3$, suitably in the presence of an organic solvent. The reagent capable of introducing a carbamoyl group may suitaly be an organic acid isocyanate. Particularly when it is desired subsequently to remove the organic acid acyl moiety to leave an unsubstituted carbamoyl group, the isocyanate used is preferably the isocyanate of a strong organic acid, that is to say, suitably an organic acid having a $pK_a$ not exceeding 3. The organic acid may suitably be a sulphonic acid or a carboxylic acid.

The isocyanate may be represented by the general formula XX:

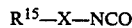   XX in which $R^{15}$ denotes the residue of an organic acid of the formula XXI:

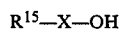   XXI and X denotes —CO— or —$SO_2$—.

The organic acid used should of course be one not containing any substitutents in the residue $R^{15}$ that are likely to interfere with the desired reaction or cause significant side reactions. Also, advantageously it should be one that will not result in the formation of acidic by-products that could interfere with subsequent reactions or with other positions of the erythromycin molecule.

Examples of suitable organic acids of the formula XXI from which the isocyanate may be derived include acetic acid, methoxyacetic acid, trichloroacetic acid, benzoic acid and p-toluenesulphonic acid.

The reaction with the isocyanate may suitably be carried out in an inert solvent. Suitable solvents include, for example, halogenated hydrocarbon solvents (for example, chloroform and dichloromethane), ether solvents (for example, tetrahydrofuran, dioxan, ethoxyethane, and 1,2-dimethoxyethane), and acetonitrile, and also mixtures of two or more such solvents. Preferred solvents are tetrahydrofuran and dichloromethane.

The reaction is advantageously carried out using a large excess of the isocyanate, that is to say suitably using from 2 to 10 moles, advantageously from 5 to 10 moles, of the isocyanate per mole of the erythromycin compound of the general formula XVI. The amount of isocyanate needed may, of course, be affected by the presence of additional reaction sites, especially additional hydroxy groups, in the erythromycin molecule.

The said reaction may suitably be effected at ambient to slightly elevated temperature, preferably at ambient temperature. The reaction may, for example, be effected at a temperature within the range of from 0° C. to 50° C., preferably from 15° C. to 30° C., especially about 20° C.

The reaction of the erythromycin compound of the general formula XVI with the isocyanate generally produces a corresponding erythromycin derivative in which the 6-position carries an N-substituted carbamoyl group of the formula VIII:

$$-O-CONH-X-R^{15} \qquad \text{VIII}$$

in which $R^{15}$ and X are defined as above. If that is the desired 6-substituent, the product thus obtained may then be worked-up as described below. If, on the other hand, it is desired to obtain an N-unsubstituted erythromycin 6-carbamate derivative according to the invention, the product containing the 6-substituent of the formula VIII may be subjected to hydrolysis in order to remove the $-X-R^{15}$ group and leave the desired 6-carbamoyloxy group. In the latter case, it has been found to be particularly convenient to use the isocyanate of trichloroacetic acid, as the trichloroacetyl group may readily be removed by hydrolysis and can, in fact, often be removed simultaneously with any formyl protecting groups.

The hydrolysis may suitably be effected under alkaline conditions, preferably mildly alkaline conditions. It is convenient to effect the hydrolysis under reflux in a mixture of methanol, water and triethylamine, optionally in conjunction with an inert organic co-solvent. It is thought to assist the desired hydrolysis step if the grouping $-X-R^{15}$ has a greater electron-withdrawing effect than does the erythromycin nucleus, and it may therefore be convenient to choose the organic acid accordingly (e.g. trichloroacetic acid).

If further conversion and/or derivatisation steps are to be carried out on the erythromycin molecule, it may be convenient to effect such steps prior to the hydrolysis and then to subject the product to hydrolysis to effect simultaneous removal of the organic acid residue $-X-R^{15}$ and of protecting groups. Hydrolysis as described above will often effect removal of protecting groups, such as the formyl protecting group.

If the initial erythromycin compound of the general formula XVI contains an unprotected 11-hydroxy group ($R^5=OH$), that group may react with the isocyanate to give an 11-(optionally substituted)-carbamoyloxy group simultaneously with the reaction at the 6-position. If, however, the starting compound also contains an unprotected 12-hydroxy group ($R^4=OH$), the resulting 11-(optionally substituted)-carbamoyloxy group may cyclise with the 12-hydroxy group to give an 11,12-cyclic carbonate ($R^4+R^5=-O-CO-O-$).

Moreover, any other unprotected hydroxy groups in the erythromycin molecule may also react with the isocyanate to form (optionally substituted)carbamoyl esters as discussed above. In some cases, such ester groups are, however, very labile and may become removed during the hydrolysis or other work-up steps.

If the initial erythromycin compound of the general formula XVI contains a 9-oxime group, that group may react with the isocyanate to form a 9-substituted-oxime, but again the carbamoyl group may become removed during later reaction steps to leave the 9-oxime. Alternatively, the 9-oxime group may first be protected, for example as discussed above, so that the carbamoylation reaction is in fact carried out on a 9-substituted-oxime.

After completion of the carbamoylation reaction, and preferably prior to removal of any protecting groups, and also preferably prior to the above-mentioned hydrolysis steps, the 9-oxo, 9-oxime or 9-substituted-oxime group may optionally be converted into another such group. If the desired product of the general formula I contains a 9-imino group, it may be obtained by conversion from a 9-oxime group, and the resulting 9-imino group may in turn, if necessary, be converted to a 9-oxo group or a 9-(optionally substituted)-amino group.

All such conversions at the 9-position may be carried out in known manner, for example as described in the above-cited references. For example, the oxime may be converted to the imine by reaction with titanium trichloride in known manner, and the imine may be converted to the amine by reaction with sodium borohydride in known manner.

Also after completion of the reaction with the isocyanate, and prior or subsequent to any conversion of the 9-substituent, any of the groups $R^5$, $R^6$, $R^8$ and $R^9$ may be converted to any of the other such groups within the definitions given above by methods known in the art, for example by the methods disclosed in the above-cited references. For example, a compound in which $R^9$ denotes hydrogen and $R^8$ denotes hydroxy can be converted to a compound in which $R^8$ and $R^9$ together denote oxo and optionally thereafter to a compound in which $R^9$ denotes hydroxy or acetoxy and $R^8$ denotes hydrogen by methods analogous to those described in U.S. Pat. No. 3,884,903, op. cit.

After completion of the reaction with the isocyanate and the subsequent hydrolysis, any remaining protecting groups (such as a benzyloxycarbonyl group) may be removed by a conventional method. It is often appropriate to employ a hydrogenation procedure.

The hydrogenation may suitably be carried out in the presence of a transition metal catalyst, for example palladium, which may, for example, be in the form of palladium on carbon (charcoal), palladium on barium sulphate, palladium on calcium carbonate, or palladium black. A favoured catalyst is palladium on carbon (sometimes referred to as palladium on charcoal); for example 5%, 10%, 20% or 30% palladium on carbon. A low, medium or high pressure of hydrogen may be used in this reaction, for example a pressure of from 1 to 6 atmospheres absolute, a pressure of 1 atmosphere absolute being convenient. The reaction may suitably be carried out at a non-extreme temperature, for example at a temperature within the range of from 0° C. to 30° C., preferably from 12° C. to 25° C. It is generally convenient to carry out the reaction at ambient temperature. The reaction is preferably carried out at a pH within the range of from 4.5 to 5.0, which may be maintained by the use of a suitable buffer, for example an acetate buffer at pH 4.8. Suitable solvents for carrying out the hydrogenation include ethanol, n-propanol, isopropanol, tetrahydrofuran, dioxan, ethyl acetate, a mixture of two or more such solvents, or such a solvent or mixture in the presence of water. A favoured solvent is ethanol.

When necessary, the dimethylamino group at the 3'-position may conveniently be restored by effecting a reductive methylation, which advantageously may be carried out at the same time as the reductive removal of the protecting groups, as in the method of Flynn et al, op. cit.

A compound of the general formula I may be converted to a pharmaceutically acceptable salt thereof or ester thereof in a conventional manner at any convenient stage in the manufacturing process, for example before or after the removal of any protecting groups and/or before or after any conversion of the 9-substituent and/or of groups $R^5$, $R^6$, $R^8$ and $R^9$ to other such groups.

Isolation and purification of a compound according to the invention may be carried out using conventional methods, and may include a chromatography step. Preferably the product is isolated in crystalline form.

The compounds according to the invention, that is to say, the compounds of the general formula I and their pharmaceutically acceptable salts and esters, have antibacterial properties and are useful for the treatment of bacterial infections in animals, especially mammals, including humans, in particular humans and domesticated animals (including farm animals). The compounds may be used for the treatment of infections caused by a wide range of gram-positive and gram-negative organisms including, for example, *Bacillus subtilis, Corynebacterium xerosis, Sarcina lutea, Staphylococcus aureus, Streptococcus faecalis, Streptococcus pyogenes, Streptococcus agalactiae, Streptococcus pneumoniae, Haemophilus sp. Neisseria sp., Chlamydia sp.,* and *Legionella sp.*

The present invention provides a pharmaceutical composition comprising a compound according to the invention together with a pharmaceutically acceptable carrier or excipient.

The present invention also provides a method of treating bacterial infections in animals, especially in humans and in domesticated mammals, which comprises administering a compound or composition according to the invention to a patient in need thereof.

The compounds and compositions according to the invention may be formulated for administration in any convenient way for use in human or veterinary medicine, by analogy with other antibiotics.

The compounds and compositions according to the invention may be formulated for administration by any route, for example oral, topical or parenteral. The compositions may, for example, be made up in the form of tablets, capsules, powders, granules, lozenges, creams, syrups, or liquid preparations, for example solutions or suspensions, which may be formulated for oral use or in sterile form for parenteral administration by injection or infusion.

Tablets and capsules for oral administration may be in unit dosage form, and may contain conventional excipients including, for example, binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; and pharmaceutically acceptable wetting agents, for example sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or another suitable vehicle before use. Such liquid preparations may contain conventional additives, including, for example, suspending agents, for example sorbitol, methyl cellulose, glucose syrup, gelatin, hydroxyethyl cellulose, carboxymethyl cellulose, aluminium stearate gel or hydrogenated edible fats; emulsifying agents, for example lecithin, sorbitan monooleate or acacia; non-aqueous vehicles (which may include edible oils), for example almond oil, oily esters (for example glycerine), propylene glycol, or ethyl alcohol; preservatives, for example methyl or propyl p-hydroxybenzoate or sorbic acid; and, if desired, conventional flavouring and colouring agents.

A compound or composition according to the invention may suitably be administered to the patient in an antibacterially effective amount.

A composition according to the invention may suitably contain from 0.1% by weight, preferably from 10 to 60% by weight, of a compound according to the invention (based on the total weight of the composition), depending on the method of administration.

The compounds according to the invention may suitably be administered to the patient at a daily dosage of from 1.5 to 50 mg/kg of body weight. For an adult human (of approximately 70 kg body weight), from 100 to 3000 mg, for example about 1500 mg, of a compound according to the invention may be administered daily. Suitably, the dosage for adult humans is from 5 to 20 mg/kg per day. Higher or lower dosages may, however, be used in accordance with normal clinical practice.

When the compositions according to the invention are presented in unit dosage form, each unit dose may suitably comprise from 25 to 1000 mg, preferably from 50 to 500 mg, of a compound according to the invention.

No adverse toxicological effects are indicated when the compounds according to the invention are administered within the above-mentioned dosage ranges.

The following examples illustrate the preparation of compounds according to the present invention. The percentage yields quoted throughout the examples are calculated on the theoretical yield from the corresponding erythromycin derivative used as the respective starting material.

EXAMPLE 1a

N-Desmethyl-N,2'-O-dibenzyloxycarbonylerythromycin A 9-benzyloxycarbonyloxime 4"-formate (2) and 11,4"-diformate (3)

To a solution of N-desmethyl-N,2'-O-dibenzyloxycarbonylerythromycin A 9-benzyloxycarbonyloxime (1) (10 g) (obtained from erythromycin A 9-oxime by treatment with benzyl chloroformate in the manner of E. H. Flynn et al, *J.Amer.Chem.Soc.*, 1955, 77, 3104–3106) and 4-dimethylaminopyridine (100 mg) in pyridine (50 ml) and ether (100 ml) was added acetic-formic anhydride (10 ml) over one hour at 0° C.; then the cooling bath was removed and the mixture was stirred at room temperature for 5½. The mixture was then worked up by addition of excess aqueous sodium hydrogen carbonate solution, evaporation to low bulk in vacuo at room temperature and partitioning the residue between ethyl acetate and water. The ethyl acetate layer was dried (MgSO$_4$) and evaporated.

The crude residue was then chromatographed on silica gel, eluting with ethyl acetate/hexane mixture 40/60.

In this way two chromatographically pure fractions were obtained.

The less polar fraction, eluted first, was the 4"-monoformate (2), an amorphous solid (2.7 g, 26%) $v$hd max (CHCl$_3$) 1750 (sh), 1730, 1690. (Found: m/e 1165 MH$^+$, calc. MW 1164; C, 63.05; H, 7.25; C$_{61}$H$_{85}$N$_3$O$_{19}$ requires C, 62.89; H, 7.22; N, 2.41).

The more polar fraction, eluted later, was the 11,4''-diformate (3) (5.0 g, 48%) $\nu_{max}$(CHCl$_3$) 1770 (sh), 1730, 1690 cm$^{-1}$. (Found: m/e 1215 MNa+, calc, MW 1192; C, 62.36; H, 6.82; N, 2.53; C$_{62}$H$_{84}$N$_2$O$_{21}$ requires C, 62.42; H, 7.05; N, 2.35%).

EXAMPLE 1b

N-Desmethyl-N,2'-O-dibenzyloxycarbonylerythromycin A 9-benzyloxycarbonyloxime 11,4''-diformate 6-trichloroacetylaminocarboxylate (4)

The diformate (3) from Example 1a (1.0 g) in dichloromethane (10 ml) was treated with a 10% solution of trichloroacetyl isocyanate in dichloromethane (3×1 ml) added at hourly intervals with stirring at room temperature. After stirring for 2 days at room temperature, methanol (3 ml) was added and the mixture was evaporated to dryness in vacuo. The residue was then rapidly chromatographed, eluting with dichloromethane/ethyl acetate mixture 4/1 giving compound (4) as an amorphous solid (0.88 g, 76%) $\nu_{max}$ (CHCl$_3$) 1800, 1730, 1690 cm$^{-1}$.

EXAMPLE 1c

N-Desmethyl-N,2'-O-dibenzyloxycarbonylerythromycin A 9-oxime 6-carbamate (5)

The trichloroacetylaminocarboxylate (4) from Example 1b (650 mg) was refluxed for 2 h with a mixture of methanol/water/triethylamine, 100/10/4 (20 ml).

The mixture was then concentrated to low bulk in vacuo and the residue partitioned between ethyl acetate and aqueous sodium hydrogen carbonate solution. The solvent layer was dried and evaporated and the residue purified by column chromatography eluting with ethyl acetate/hexane 4/1 to give a chromatographically pure product (5) (250 mg, 51%) $\nu_{max}$ (CHCl$_3$) 3510, 3400, 1730(b), 1700 cm$^{-1}$; (Found: MH+1046, C$_{53}$H$_{79}$N$_3$O$_{18}$ requires MW 1045). (Found: C, 60.02; H, 7.56; N, 3.91%. C$_{53}$H$_{79}$N$_3$O$_{18}$ requires C, 60.86; H, 7.54; N, 4.02%).

EXAMPLE 1d

Erythromycin A 9-oxime 6-carbamate (6)

N-Desmethyl-N-2'-O-dibenzyloxycarbonyl erythromycin A 9-oxime 6-carbamate (5) from Example 1c (150 mg) dissolved in ethanol (10 ml) and pH 4 acetate buffer (1.0 ml) was hydrogenated over 10% palladium-charcoal (20 mg) for 30 min. A 40% aqueous formaldehyde solution (1 ml) was then added, and hydrogenation was continued for a further 1½h. The catalyst was then filtered off. Aqueous 10% sodium carbonate was added to bring the pH to ca. 10–11 and the mixture was concentrated to low bulk in vacuo. The residue was partitioned between ethyl acetate and water, extracting three times with ethyl acetate. The solvent layer was dried (MgSO$_4$) and evaporated to give the pure 6-carbamate (6) (105 mg, 92%) as a white amorphous solid; $\nu_{max}$ 3530, 3500, 1725(b), 1600(w) cm$^{-1}$ [$\alpha$]$_D^{20}$ (1% wt/vol in CHCl$_3$)−80.0°, (Found: m/e 791.4794, C$_{30}$H$_{69}$N$_3$O$_{14}$ requires 791.4783).

EXAMPLE 2a

N-Desmethyl-N,2'-O-dibenzyloxycarbonylerythromycin A 9-oxime 6-carbamate 11,12-carbonate (7)

The monoformate (2) from Example 1a (500 mg) in dichloromethane (5 ml) was treated with a 10% solution of trichloroacetyl isocyanate in dichloromethane (3 x 0.5 ml) added over ½ h at room temperature. After stirring for 24 h at room temperature, methanol (2 ml) was added and the mixture was evaporated to dryness in vacuo.

The crude residue was then refluxed for 2 h with a mixture of methanol/water/triethylamine 100/10/4 (20 ml) and finally concentrated to low bulk in vacuo. The residue was partitioned between ethyl acetate and aqueous sodium hydrogen carbonate solution and the solvent layer dried (MgOS$_4$) and evaporated to dryness in vacuo.

On silca gel chromatography, eluting with ethyl acetate/hexane mixtures, a chromatographically pure product (7) was obtained as an amorphous white solid (78 mg, 11%), $\nu_{max}$ (CHCl$_3$) 3540, 3430, 1810, 1740, 1700, 1590 (w) cm$^{-1}$. (Found; m/e MH+1072, C$_{54}$H$_{77}$N$_3$O$_{19}$ requires MW 1071).

EXAMPLE 2b

Erythromycin A 9-oxime 6-carbamate 11,12-carbonate (8)

N-Desmethyl-N,2'-O-dibenzyloxycarbonylerythromycin A 9-oxime 6-carbamate 11,12-carbonate (7) (150 mg) dissolved in ethanol (120 ml) and pH 4 acetate buffer (1 ml) was hydrogenated over 10% palladium-charcoal (20 mg) for 1 h at 14° C. Aqueous 40% formaldehyde solution (1 ml) was added and hydrogenation was continued for a further 1 h. The product was then worked up as in Example 1d to give an amorphous white solid (115 mg, 100%) $\nu_{max}$ (CHCl$_3$) 3590, 3530, 3410, 1810, 1730, 1590 (w) cm$^{-1}$ (Found: m/e 817.4556, C$_{39}$H$_{67}$N$_3$O$_{15}$ requires MW =817.4575) [$\alpha$]$_D^{20}$ (1% wt/vol in CHCl$_3$) −18.0°.

EXAMPLE 3

Erythromycin A 6-carbamate (10)

Erythromycin A 2',4''-diformate (9) (1.0 g) in dichloromethane (2 ml) was treated with a 20% solution of trichloroacetyl isocyanate in dichloromethane (3 ml) over 1½h. After stirring overnight at room temperature, the mixture was worked up and hydrolysed as in Example 2a. The crude product was chromatographed on silica gel, eluting with dichloromethane/methanol/0.880 ammonia 50/10/1. The major pure fraction gave on evaporation a white crystalline solid (170 mg, 17%) m.p. 225°-227° C. ex. chloroform/hexane. $\nu_{max}$ (CHCl$_3$) 3500, 3400, 1720, 1590 (w) cm$^{-1}$ [$\alpha$]D$^{20}$ (1% wt/vol in MeOH) −76.5°.

EXAMPLE 4a

Erythromycin A 9-methoxime 2',4'-diformate (12)

To a solution of erythromycin A 9-methoxime (11) (1.0 g) and 4-dimethylaminopyridine (10 mg) in dry pyridine (5 ml) and dry ether (10 ml) was added acetic-formic anhydride (1 ml) over 10 min at 20° C. The mixture was stirred overnight, then aqueous sodium hydrogen carbonate solution (5 ml, saturated) was added and the mixture was rapidly evaporated to low bulk at 20° C. in vacuo. The residue was then immediately partitioned between ethyl acetate and water, and the organic layer was dried (MgSO$_4$) and evaporated to dryness in vacuo.

The residual product (12) was a white amorphous solid (0.95 g). [Note: This compound has not been characterised as it decomposes on column chromatography to give pure erythromycin 9-methoxime 4''-formate. However $_1$H n.m.r. of the crude (12) shows two clear 1H singlets for the two formate groups at δ8.2 and δ 8.15].

This product was suitable for further reaction without additional purification.

EXAMPLE 4b

Erythromycin A 9-methoxime 6,11-dicarbamate (13) and erythromycin A 9-methoxime 11,12-carbonate 6-carbamate (14)

Erythromycin 9-methoxime 2',4"-diformate (12), (550 mg, prepared as in Example 4a) in dichloromethane (4 ml) was treated with a 20% solution of trichloroacetyl isocyanate in dichloromethane (1 ml). After 1.5 h a further portion (1 ml) of this solution was added and the reaction mixture was stirred at room temperature overnight.

It was then worked up and hydrolysed as in Example 2a.

The crude product was then chromatographed on silica gel eluting with dichloromethane/methanol/0.880 $NH_3$ (100/10/1).

In this way were obtained two products. The less polar fraction, eluted first from the column, was erythromycin A 9-methoxime 11,12-carbonate 6-carbamate, a white amorphous solid (14), (251 mg, 45%) $v_{max}$ $CHCl_3$) 3510, 3400, 1800, 1730(b), 1580 $[\alpha]D_{20}(CHCl_3)$ −35.6. (Found: m/e 854 for MNa+, $C_{40}H_{69}N_3O_{15}$ requires MW 831). The next pure fraction to be eluted from the column was the more polar erythromycin A 9-methoxime 6,11-dicarbamate, also a white amorphous solid (13), (97 mg, 18%) $v_{max}$ ($CHCl_3$) 3500, 3430, 3350, 1725(b), 1600, 1580 $[\alpha]_D^{20}$ (1% wt/vol in $CHCl_3$) −87.9°. (Found: $MH^{30}$ 849, $C_{40}H_{72}N_4O_{15}$ requires MW 848).

EXAMPLE 5

Erythromycylamine 6-carbamate (16)

Erythromycin A 9-oxime 6-carbamate (6) (from Example 1d) (444 mg) in methanol (10 ml) with ammonium acetate (2.0 g) was treated with titanium trichloride solution (15% in water, 2.0 ml) under nitrogen at 20° C. After stirring for 2 h at this temperature the mixture was made alkaline with aqueous sodium carbonate and was then extracted with two portions of 20 ml ether. The combined ether extracts were dried ($MgSO_4$) and evaporated, then the residue was redissolved in methanol (4 ml). To this methanolic solution of erythromycin A 6-carbamate 9-imine (15) was then added sodium borohydride (20 mg) and the mixture was stirred for 30 min at 20° C. and was then evaporated to low bulk at room temperature.

The residue was dissolved in water (20 ml), brought to pH 2.5 by the addition of citric acid and kept at that pH for 5 min.

The pH was then successively raised to 6, 7, 8, 9 and finally 10.5 by the addition of aqueous sodium carbonate and at each pH value the aqueous solution was extracted with dichloromethane. At pH 6 and 7 the extracts contained mainly unchanged oxime as revealed by t.l.c. (dichloromethane/methane/0.880 ammonia, 200/30/3). At pH 8, 9 and 10.5 the extract was the desired amine (16) which was then purified by silica gel chromatogaphy, eluting with dichloromethane/methanol/0.880 ammonia (from 200/10/1 to 200/30/3). In this way the pure amine (16) was obtained (89 mg, 20%) $v_{max}$ ($CHCl_3$) 3620, 3500, 1710, 1595 cm$^{-1}$ $[\alpha]_D^{20}$ (1% wt/vol in $CHCl_3$) −44.9°. (Found: MNa+800, corresponds to MW 777, $C_{38}H_{71}N_3O_{13}$ requires 777).

EXAMPLE 6

Erythromycin A 6-carbamate 11,12-carbonate (17)

Erythromycin A 2',4"-diformate (9) (1.0 g) in dichloromethane (4 ml) was cooled to −20° C. and trichloroacetyl isocyanate (0.32 ml, 0.47 g, 2 eq.) was added. The temperature was then allowed to reach −5° C. over a period of 2 h. The mixture was then worked up and hydrolysed as in Example 2a. The crude product was a mixture from which only one compound was isolated pure by silica gel chromatography, eluting with dichloromethane/methanol/0.880 ammonia 100/10/1, (260 mg) (25%). This was the desired 6-carbamate 11,12-carbonate (17) $v_{max}$ ($CHCl_3$) 3505, 3400, 1800, 1730, 1580 cm$^{-1}$ $[\alpha]^{20}D$ (1% in $CHCl_3$) −23.9°. (Found: MNa+825, corresponds to MW 802, $C_{39}N_{66}N_2O_{15}$ requires 802).

EXAMPLE 7a

N-Desmethyl-N,2'-O-dibenzyloxycarbonylerythromycin A 9-methoxime 4",11-diformate (19)

To a solution of N-desmethyl-N,2'-O-dibenzyloxycarbonylerythromycin A 9-methoxime (18) (3.0 g), obtained from erythromycin A 9-oxime by treatment with benzyl chloroformate in the manner of E. H. Flynn et al, (*J. Amer. Chem. Soc.*, 1955, 77, 3104–3106) and 4-dimethyl- aminopyridine (0.38 g) in dichloromethane (20 ml) and triethylamine (10 ml) at −50° C. was added acetic-formic anhydride (1 ml) over 5 min. The reaction mixture was then allowed to reach −30°C. over ½ h. Methanol (5 ml) was then added. The mixture was allowed to reach room temperature then excess of saturated sodium hydrogen carbonate solution was added and the mixture was evaporated to low bulk in vacuo. The residue was partitioned between ethyl acetate and water then the organic layer was further washed with aqueous citric acid solution, again with sodium hydrogen carbonate solution and finally dried ($MgSO_4$) and evaporated.

The product was purified by silica gel chromatography, eluting with ethyl acetate/hexane mixtures to give pure N-desmethyl-N,2'-O-dibenzyloxycarbonylerythromycin A 9-methoxime 4",11-diformate (19) as an amorphous white solid (2.0 g, 64%) $v_{max}$ 3550, 1720, 1680 cm$^{31\ 1}$. (Found: MNa+1095, corresponds to MW 1072. $C_{55}H_{80}N_2O_{19}$ requires 1072).

EXAMPLE 7b

N-Desmethyl-N,2'-O-dibenzyloxycarbonylerythromycin A 6-carbamate 9-methoxime (20) and N-desmethyl-N,2'-O-dibenzyloxycarbonylerythromycin A 6,12-dicarbamate 11-formate 9-methoxime (21)

To a solution of N-desmethyl-N,2'-O-dibenzyloxycarbonylerythromycin A 9-methoxime 4",11-diformate (19) (1.11 g) in dichloromethane (10 ml) at −40° C. was added trichloroacetyl isocyanate (0.16 ml, 0.24 g, 1.2 equiv.). After 1 h the mixture was transferred to a freezer and kept at −15° C. overnight. The mixture was then worked up in exactly the same way as after the formylation reaction in Example 7a, to give a crude amorphous white product.

This was then refluxed with methanol/water/triethylamine mixture 90/10/4 for 1 h (no further change on tlc) then the product was isolated by evaporation, partition (EtOAc/water), and then drying and re-evaporating the organic layer.

Silica gel chromatography (eluting with ethyl acetate/hexane mixtures) gave as a major fraction the desired N-desmethyl-N,2'-O-dibenzyloxycarbonyl erythromycin A 6-carbamate 9-methoxime (20) as a white amorphous solid, (158 mg, 51%) $v_{max}$ (CHCl$_3$) 3500, 3370, 1735, 1715, 1690, 1590 cm$^{-1}$. (Found: m/e 1060 MH$^+$· $C_{54}H_{81}N_3O_{18}$ requires , MW 1059). From the same chromatography was also obtained as a more polar fraction N-desmethyl-N,2'-O-dibenzyloxycarbonylerythromycin A 6,12-dicarbamate 11-formate 9-methoxime (21) (128 mg, 11%) as a white amorphous solid. (Found: MNa$^+$1153, corresponds to MW 1130. $C_{56}H_{82}N_4O_{20}$ requires 1130).

EXAMPLE 7c

Erythromycin A 6-carbamate 9-methoxime (22)

N-Desmethyl-N,2'-O-dibenzyloxycarbonyl erythromycin A 6-carbamate 9-methoxime (20) (796 mg) was subjected to reductive formylation by the method of Example 1d. In this way was obtained the desired product (22) (600 mg, 99%) as a white amorphous solid $v_{max}$ (CHCl$_3$) 3500, 3370, 1715, 1595 cm$^{-1}$, $[\alpha]_D^{20}$ (1% wt/vol in CHCl$_3$) −81.9°. (Found: m/e 805.4942, $C_{39}H_{71}N_3O_{14}$ requires 805.4937).

EXAMPLE 7d

Erythromycin A 6,12-dicarbamate 11-formate 9-methoxime (23)

By exactly the same method as in Example 7c, N-desmethyl-N,2'-O-dibenzyloxycarbonylerythromycin A 6,12-dicarbamate 11-formate 9-methoxime (21) (180 mg) was converted to erythromycin A 6,12-dicarbamate 11-formate 9-methoxime (23) (85 mg, 61%) after purification by silica gel chromatography, eluting with dichloromethane/methanol/880 ammonia 100/10/1. The product was a white solid $v_{max}$(CHCl$_3$) 3500, 3420, 3360, 1720, 1590, 1575 cm$^{-1}$ $[\alpha]_D^{20}$ (1% w/v in CHCl$_3$) −70.0°. (Found: MH$^+$877, $C_{41}H_{72}N_4O_{16}$ requires 876).

EXAMPLE 8a

N-Desmethyl-N,2'-O-dibenzyloxycarbonylerythromycin A 9-(2-methoxyethoxymethoxime) (24)

N-Desmethyl-N,2'-O-dibenzyloxycarbonylerythromycin A 9-benzyloxycarbonyloxime (1) (3.0 g) was refluxed for 2 h with methanol/water/triethylamine mixture 100/10/4 40 ml). The solvent was evaporated in vacuo and the residue was partitioned between EtOAc/aqueous sodium hydrogen carbonate solution. The organic layer was dried (MgSO$_4$) and evaporated to give the free oxime (2.78 g) in a nearly pure state.

This was dissolved in dimethylformamide (40 ml) and stirred at 20° C. with finely ground potassium carbonate (2.2 g) and 50% sodium hydride suspension in liquid paraffin (166 mg) for 5 min. 2-Methoxyethoxymethyl chloride (2.8 ml) was then added and stirring was continued for 30 min. The mixture was then diluted with ethyl acetate and washed with water. The organic layer was evaporated and the residue purified by silica gel chromatography eluting with dichloromethane/ethyl acetate 1/1. In this way the pure product (24) was obtained as a white solid (1.2 g, 38%).

EXAMPLE 8b

N-Desmethyl-N,2'-O-dibenzyloxycarbonylerythromycin A 4'', 11-diformate 9-(2-methoxyethoxymethoxime) (25) and
N-desmethyl-N,2'-O-dibenzyloxycarbonylerythromycin A 4''-formate 9-(2-methoxyethoxymethoxime) (26)

To the methoxyethoxymethoxime (24) prepared in Example 8a (750 mg), 4-dimethylaminopyridine (92 mg, 1.1 eq.) and formic acid (0.25 ml, 7 eq.) in triethylamine (2.5 ml, excess and dichloromethane (50 ml) cooled to −15° C. was added acetic anhydride (2 ml, excess) over 30 min. The temperature was then raised to 0° C. for 1 h then methanol (10 ml) was added and the reaction mixture was worked up as in Example 7a.

On silica gel chromatography the first major fraction eluted using ethyl acetate/hexane mixtures was the 4''-monoformate (26) (342 mg, 44%) $v$ max (CHCl$_3$) 3450(b), 1720, 1680 cm$^{-1}$. (Found: MNa$^+$1141, corresponds to MW 1118. $C_{58}H_{86}N_2O_{21}$ requires 1118). The next major (fraction eluted was the desired 4'', 11-diformate (25) (222 mg, 28%) $v$ max (CHCl$_3$) 3550, 3420, 1720, 1680 cm$^{-1}$. (Found: MNa$^+$1169, corresponds to MW 1146. $C_{57}H_{86}N_2O_{21}$ requires 1146).

EXAMPLE 8c

N-Desmethyl-N,2'-O-dibenzyloxycarbonylerythromycin A 6-carbamate 9-(2-methoxyethoxymethoxime) (28)

The diformate (25) of Example 8b (500 mg) in dichloromethane (5 ml) was treated at 20° C. with trichloroacetyl isocyanate (0.052 ml, 0.077 g, 1.1 eq.). After 1 h at 20° C. a further portion of trichloroacetyl isocyanate (0.052 ml) was added and the mixture again stirred 1 h. It was then worked up as in the formylation experiment in Example 7a to give a crude product which was purified by silica gel chromatography eluting with ethyl acetate/hexane mixtures to give N-desmethyl-N,2'-O-dibenzyloxycarbonylerythromycin A 4'',11-diformate 9-(2-methoxyethoxymethoxime) 6-trichloroacetyl carbamate (27) as a white solid (220 mg). This product was then refluxed with methanol/water/triethylamine 100/10/4 (20 ml) for 2 h and was then worked up as in Example 7b. The product after silica gel chromatography was a white solid (28) (145 mg, 81%) $v_{max}$(CHCl$_3$). 3500, 3470, 1730/1720, 1690, 1590 cm$^{-1}$· (Found: MH+1134, $C_{57}H_{87}N_3O_{20}$ requires MW 1133).

EXAMPLE 8d

Erythromycin A 6-carbamate 9-(2-methoxyethoxymethoxime) (29)

By the same method as in Example 1d N-desmethyl-N,2'-O-dibenzyloxycarbonylerythromycin A 6-carbamate 9-(2methoxyethoxymethoxime) (28) (140 mg) was converted into erythromycin A 6-carbamate 9-(2-methoxyethoxymethoxime) (29) (100 mg, 92%) as a white solid $v_{max}$ (CHCl$_3$) 3500, 3370, 1715, 1590 cm$^{-1}$ $[\alpha]_D^{20}$ (2% w/v in CHCl$_3$) −74.3°. (Found; M/W 879.5349, $C_{42}H_{77}N_3O_{16}$ requires MW 879.5306).

EXAMPLE 9a

N-Desmethyl-N,2'-O-dibenzyloxycarbonylerythromycin A 6-benzoylcarbamate 9-oxime (30) and
N-Desmethyl-N,2'-O-dibenzyloxycarbonylerythromycin A 6-benzoylcarbamate 11,12-carbonate 9-oxime (31)

The diformate (3) of Example 1a (500 mg) in dichloromethane (3 ml) at −30° C. was treated with (10%)

benzoyl isocyanate in dichloromethane (0.75 ml) (1.2 eq.). The mixture was kept at −15° C. for 3 h and then gradually allowed to reach ambient temperature overnight. It was then re-cooled to −30° C., a further portion (0.4 ml) of the reagent solution was added and the slow warming process was repeated as above. Finally the reaction mixture was worked up as in formylation experiment in Example 7a. The crude product was separated by silica gel chromatography eluting with ethyl acetate/hexane mixtures into two major fractions, a less polar fraction (147 mg) eluted first and a more polar (187 mg) eluted later. These two fractions were separately hydrolysed with methanol/water/triethylamine mixture as in Example 8c to given respectively N-desmethyl-N,2′-O-dibenzyloxycarbonylerythromycin A 6-benzoylcarbamate 9-oxime (30) (130 mg, 31%) $\nu$ max (CHCl$_3$), 3520, 3400, 1735/1720, 1670, 1470 cm$^{-1}$. (Found: MNa$^+$ 1172, corresponding to MW 1149, C$_{60}$H$_{83}$N$_3$O$_{19}$ requires MW 1149) and N-desmethyl-N,2′-O-dibenzyloxycarbonylerythromycin A 11,12-carbonate 6-benzoylcarbamate 9-oxime (31) (170 mg, 35%) $\nu_{max}$ (CHCl$_3$). 3350, 3400, 1800, 1780, 1735, 1680 cm$^{-1}$. (Found: MNa$^+$1198, corresponds to MW 1175, C$_{61}$H$_{81}$N$_3$O$_{20}$ requires 1175).

EXAMPLE 9b

Erythromycin A 6-benzoylcarbamate 9-oxime (32)

By the same method as in Example 7b N-desmethyl-N,2′-O-dibenzyloxycarbonylerythromycin A 9-oxime (30) (265 mg) was converted into erythromycin A 6-benzoylcarbamate 9-oxime (32) a white solid (129 mg, 62%) $\nu_{max}$ (CHCl$_3$) 3550(b), 3350(b), 1780, 1730, 1680(b), 1740 cm$^{-1}$. $[\alpha]_D^{20}$ (1% in CHCl$_3$)−57.7°. (Found: MN$^+$918, corresponds to MW 895, C$_{45}$H$_{73}$N$_3$O$_{15}$ requires 895).

EXAMPLE 9c

Erythromycin A 6-benzoylcarbamate 11,12-carbonate 9-oxime (33)

By the same method as in Example 1d, N-desmethyl-N,2′-O-dibenzyloxycarbonylerythromycin A 6-benzoylcarbamate 11,12-carbonate 9-oxime (31) (250 mg) was converted into erythromycin A 6-benzoylcarbamate 11,12-carbonate 9-oxime (33), which after silica gel chromatography, eluting with dichloromethane/methanol/0.880 ammonia (100/10/1), was obtained as a white solid (74 mg, 38%) $\nu_{max}$ (CHCl$_3$) 3570, 3510, 1420(b), 1810, 1790, 1740, 1480 cm$^{-1}$. (Found: MNa$^+$944, corresponds to MW 921, C$_{46}$H$_{71}$N$_3$O$_{16}$ requires 921).

EXAMPLE 10a

N-Desmethyl-N,2′-O-dibenzyloxycarbonylerythromycin A 6-benzoylcarbamate 9-methoxime (34) and N-desmethyl-N,2′-O-dibenzyloxycarbonylerythromycin A 6-benzoylcarbamate 11,12-carbonate 9-methoxime (35)

N-Desmethyl-N,2′-O-dibenzyloxycarbonylerythromycin A 4″,11-diformate (19) of Example 7a (1.0 g) in dichloromethane (6 ml) was treated as in Example 9a and the crude product was hydrolysed with methanol/water/triethylamine as in Example 8c. Silica chromatography of the product, eluting with ethyl acetate/hexane mixtures gave two main fractions. The less polar was N-desmethyl-N,2′-O-dibenzyloxycarbonylerythromycin A 6-benzoylcarbamate 9-methoxime (34), obtained as a white solid (70 mg, 7%) $\nu_{max}$ (CHCl$_3$) 3500, 3400, 1770, 1720, 1680/1670, 1480 cm$^{+1}$. (Found: MNa+1186, corresponds to MW 1163, C$_{61}$H$_{85}$N$^{30}$$_{19}$ requires 1163).

The more polar fraction was N,2′-O-dibenzyloxycarbonylerythromycin A 6-benzoylcarbonate 11,12carbonate 9-methoxime (35), obtained as a white solid (270 mg, 24%) $\nu_{max}$ (CHCl$_3$) 1800, 1770, 1730, 1670, 1470 cm$^{-1}$. (Found: MNa+1212, corresponds to MW 1189, C$_{62}$H$_{83}$N$_3$O$_{20}$ requires 1189).

EXAMPLE 10b

Erythromycin A 6-benzoylcarbamate 11,12-carbonate 9-methoxime (36)

By the same method as in Example 1d, N-desmethyl-N,2′-O-dibenzyloxycarbonylerythromycin A 6-benzoylcarbamate 11,12-carbonate 9-methoxime (35) (270 mg) was converted into erythromycin A 6-benzoylcarbamate 11,12-carbonate 9-methoxime (36) as a white solid (110 mg, 51% ) after silica gel chromatography eluting with dichloromethane/methanol/0.880 ammonia (100/10/1) $\nu_{max}$ (CHCl$_3$) 3500, 3400, 1800, 1780, 1730, 1470 cm$^{-1}$ $[\alpha]_D^{20}$ (1% CHCl$_3$) +16.8°. (Found: MNa+936, C$_{47}$H$_{73}$N$_3$O$_{16}$ requires 935).

EXAMPLE 10c

Erythromycin A 6-benzoylcarbamate 9-methoxime (37)

By the same method as in Example 1d N-desmethyl-N,2′-O-dibenzyloxycarbonylerythromycin A 6-benzoylcarbamate 9-methoxime (34) (190 mg) was converted into erythromycin A 6-benzoylcarbamate 9-methoxime (37) as a white solid after purification by chromatography eluting with dichloromethane/methanol/0.880 ammonia 100/10/1) (80 mg, 54%) $\nu_{max}$ (CHCl$_3$) 3500, 3350, 1760, 1720, 1470 cm$^{-1}$ $[\alpha]^{20}$D (1% CHCl$_3$) −76.6° (Found: MNa+932. C$_{46}$H$_{75}$N$_3$O$_{15}$ requires MW 909).

EXAMPLE 11a

N-Desmethyl-N,2′-O-dibenzyloxycarbonylerythromycin A 6,12-bis(acetylcarbamate) 11,4″-diformate 9-methoxime (38)

The diformate (19) of Example 7a (518 mg) in dichloromethane (3 ml) was treated with a 12% solution of acetyl isocyanate in dichloromethane (0.4 ml, 1.2 eq) at −15° C. The mixture was then stirred 3 h at 20° C. It was again cooled to −15° C. and a further portion (0.4 ml, 1.2 eq.) of acetyl isocyanate solution was again added. Finally the mixture was stirred at 20° C. overnight. The product was then isolated as in Example 9a. The product (38) was a white solid (424 mg, 95%) $\nu$ max (CHCl$_3$) 3400, 3250(b), 1730, 1690, 1460 cm$^{-1}$.

EXAMPLE 11b

Erythromycin A 6,12-bis-acetylcarbamate 11-formate 9-methoxime (39) and erythromycin A 6-acetylcarbamate 11,12-carbonate 9-methoxime (40)

N-Desmethyl-N,2′-O-dibenzyloxycarbonyl erythromycin A 6,12-bis(acetylcarbamate) 11,4″-diformate 9-methoxime (38) (420 mg) was hydrolysed by the method of Example 1c, and then the product was treated by the method of Example 1d to give two compounds which were separated by silica gel chromatography eluting with dichloromethane/methanol/0.880 ammonia mixture (100/10/1). The less polar product was erythromycin A 6-acetylcarbamate 11,12-carbonate 9-methoxime (40), a white solid (50 mg, 17%) $\nu_{max}$ (CHCl$_3$) 3400(b) 1800, 1770, cm$^{-1}$ [α]$_D^{20}$ (1% in CHCl$_3$)+17.9° (Found: MH+874, C$_{42}$H$_{71}$N$_3$O$_{16}$ requires MW 873). The more polar product was erythromycin A 6,12-bis(acetylcarbamate) 11-formate 9-methoxime (39) (100 mg, 31%) $v_{max}$ (CHCl$_3$) 3000, 3300(b), 1740, 1695 cm$^{-1}$. [α]$_D^{20}$ (1% in CHCl$_3$)−46' (Found: MNa+983 corresponds to MW 960, C$_{45}$H$_{76}$N$_4$O$_{18}$ requires 960).

EXAMPLE 12a

9-Dihydro-9,11-ethylideneerythromycin A 2',4''-diformate (42)

A solution of 9-dihydro-9,11-ethylideneerythromycin A (41) (0.6 g, 0.79 mmol) prepared as described in Example 9 of EP 0 184 921 A2, 4-dimethylaminopyridine (12 mg) and triethylamine (4 ml) in dichloromethane (15 ml) was treated at −25° C. with acetic formic anhydride (0.9 ml). The reaction was stirred between −25° C. and −20° C. for 1 h, then at 0° C. for a further 1 h.

The mixture was diluted with ether and washed at 0° C. with aqueous saturated sodium hydrogen carbonate. The organic layer was dried (MgSO$_4$) and concentrated under reduced pressure to yield the diformate (42) as a white foam (0.65 g) $v_{max}$3540(sh), 3430, 1720 cm$^{-1}$. (Found: m/e MH+818, C$_{41}$H$_{71}$NO$_{15}$ requires MW 817 [α]$_D^{20}$ (1% CHCl$_3$) −28.2°.

EXAMPLE 12b

9-Dihydro-9,11-ethylideneerythromycin A 6-carbamate (43)

9-Dihydro-9,11-ethylideneerythromycin A 2',4''-diformate (42) (0.65 g) was carefully dried by twice dissolving in toluene (20 ml) and re-evaporating under reduced pressure. The dried diformate was then taken up in dry tetrahydrofuran (10 ml) and cooled to -20° C. under nitrogen. Trichloroacetylisocyanate (100 μl, 1 eq.) was then added dropwise. The reaction mixture was maintained at −20° C. for 20 h, then methanol (0.1 ml) was added and the solvent removed under reduced pressure. The crude product was hydrolysed by treatment with methanol/water/triethylamine (100/10/4) for 2h at 20° C. followed by 1 h at reflux. After removal of the solvent, chromatography on silica gel eluting with ether/methanol/0.880 ammonia (90/10/1) yielded the desired 6-carbamate (43) (160 mg) as well as some less polar recovered starting material (130 mg). The yield of 6-carbamate (43) was 34% from (41) allowing for starting material recovered. The product was a white amorphous solid $v_{max}$ (CHCl$_3$) 3530, 3400, 1800(w), 1720, 1580 cm$^{-1}$. (Found: m/e MH+805, C$_{40}$H$_{72}$N$_2$O$_{14}$ requires MW 804 [α]D$^{20}$ (1% CHCl$_3$) −56.4°.

Example 13

Erythromycin A 6-methoxyacetylcarbamate 11,4''-diformate 9-methoxime (44) and erythromycin A 6,12-bis-methoxyacetylcarbamate 11,4''-diformate 9-methoxime (45)

A solution of methoxyacetyl isocyanate in dichloromethane was prepared by stirring methoxyacetyl chloride (119 mg) in dichloromethane (5 ml) at 20° C. for 20 h with silver cyanate (200 mg).

To a solution of N-desmethyl-N,2'-O-dibenzyloxycarbonylerythromycin A 9-methoxime 4'',11-diformate (19) (500 mg) in dichloromethane (3 ml) at −15° C. was added 2.5 ml of the above described methoxyacetyl isocyanate solution. The mixture was then allowed to reach 20° C. and was stirred at room temperature for one week. The mixture was then wrked up as in the formylation experiment in Example 7a to give a crude amorphous white solid.

Column chromatography on silica gel eluting with ethyl acetate/hexane mixtures separated the product (132 mg) from the less polar unchanged starting material (252 mg). The product fraction was subjected to reductive formylation by the method of Example 1d. In this way were obtained two products, separated by chromatography on silica gel, eluting with dichloromethane/methanol/0.880 ammonia 100/10/1 —both were obtained as amorphous white solids.

The first eluted product was erythromycin A 6-methoxyacetylcarbamate 11,4''-diformate 9-methoxime (44) (29 mg), $v_{max}$ (CHCl$_3$) 3400, 1790(w), 1730, 1480, 1460 cm$^{-1}$ [α]$^{20}$D (1% in CHCL$_3$) −57.2°. (Found: m/e MH+934, C$_{44}$H$_{75}$N$_3$O$_{18}$ requires 933). The next eluted product was erythromycin A 6,12-bismethoxyacetylcarbamate 11,4''-diformate (45) (35 mg) $v_{max}$ (CHCl$_3$) 3400, 3200(b), 1790, 1740-1715, 1480, 1460 cm$^{-1}$, [α]$^{20}$D (1% in CHCl$_3$) −52.7° (Found: m/e MH+1049, C$_{48}$H$_{80}$N$_4$O$_{21}$ requirs 1048).

Example 14

N-Desmethyl-N,2'-O-dibenzyloxycarbonylerythromycin A 6-p-toluenesulphonylcarbamate 11,4''-diformate 9-methoxime (46) and
N-desmethyl-N,2'-O-dibenzyloxycarbonylerythromycin A 6,12-bis-p-toluenesulphonylcarbamate 11,4''-diformate 9-methoxime (47)

To a solution of N-desmethyl-N,2'-O-dibenzyloxycarbonylerythromycin A 9-methoxime 4'',11-diformate (19) (500 mg) in dichloromethane at −40° C. was added p-toluenesulphonyl isocyanate (0.16 ml). The mixture was allowed to reach room temperature over 1 h and was then stirred for 20 h and worked up as in Example 7a. Silica gel chromatography of the crude product, eluting with ethyl acetate/hexane mixtures gave successively: unchanged starting material (19) (142 mg); the 6-p-toluenesulphonylcarbamate (46) (60 mg), $v_{max}$ cm$^{-1}$ (Found: MNa+2 1314 using F.A.B/NaOAc, corresponding to MW 1269, C$_{63}$N$_{87}$N$_3$O$_{22}$S requires 1269); and finally, the 6,12-bis-p-toluenesulphonylcarbamate (47) (153 mg), $v_{max}$ (CHCl$_3$) 3400(w), 1466, 1740, 1700 cm$^{-1}$.

The above products (46) and (47) could be deprotected by the reductive formylation method of Example 1d to give erythromycin A 6-p-toluenesulphonylcarbamate 11,4''-diformate 9-methoxime (48) and erythromycin A 6,12-bis-p-toluenesulphonylcarbamate 11,4''-diformate 9-methoxime (49).

Example 15a

11-O[2-Benzoyloxyethoxymethyl]-2'-O,N-dibenzyloxycarbonyl-des-N-methylerythromycin A 9-benzyloxycarbonyloxime (50)

2'-O,N,dibenzyloxycarbonyl-des-N-methylerythromycin A 9-benzyloxycarbonyloxime (1) (3.24 g) in dry dimethylformamide (20 ml) was treated with 2,6-lutidine (1.75 ml) and 1-benzoyloxy-2-(chloromethoxy)ethane (1.93 ml) and the mixture stirred at room temperature for 24 h. The solution was diluted with ethyl acetate (150 ml) and the organic solution washed successively with water, citric acid solution, aqueous sodium bicarbonate solution, and finally brine. After drying over anhydrous magnesium sulphate, the solvent was evaporated. Chromatography of the residue on silica gel using ethyl acetate/dichloromethane (1:2) as eluent gave the title product (50) as a colourless foam (3.56 g); $\nu_{max}$ (CHCl$_3$) 1720 cm$^{-1}$.

Example 15b

11-O-[2-Benzoyloxyethoxymethyl]-N-desmethyl-N,2'-O-dibenzyloxycarbonylerythromycin A 4''-formate (51)

11-O-[2-Benzoyloxyethoxymethyl-N-desmethyl-N,2'-O-dibenzyloxycarbonylerythromycin A (50) (131 mg) was treated with formic-acetic anhydride as in Example 1a to give the title compound (51) (112 mg, 84%) after silica gel chromatography eluting with 3% methanol in dichloro methane. $\nu_{max}$ 3500, 1730 cm$^{-1}$ (Found: m/e MNa$^+$1365, C$_{71}$N$_{94}$N$_2$O$_{23}$ requires MW 1342).

Example 15c

11-O-(2-Benzoyloxyethoxymethyl)-N-desmethyl-N,2'-O-dibenzyloxycarbonylerythromycin A 6-trichloroacetylcarbamate 4''-formate 9-benzyloxycarbonyloxime (52)

11-O-[2-Benzoyethoxymethyl]-N-desmethyl-N,2'-O-dibenzyloxycarbonyl erythromycin A 4''-formate (51) (1.44 g) in dichloromethane (15 ml) at 0° C. was treated with trichloroacetyl isocyanate (0.135 ml) in dichloromethane (5 ml) followed after 3 h by a further portion (0.034 ml) of trichloroacetyl isocyanate. The mixture was then treated as in Example 1b to give the title compound (52) (500 mg, 37%) after rapid chromatography on silica gel eluting with dichloromethane/methanol 100/1. $\nu_{max}$ (CHCl$_7$) 3500, 3400, 1800, 1720, 1590 cm$^{-1}$. (Found: M−H+Na$^+$$_2$ 1574 C$_{74}$H$_{94}$Cl$_3$N$_3$O$_{25}$ requires MW 1529.

Example 15d

11-O-(2-Hydroxyethoxymethyl)-N-desmethyl-N,2'-O-dibenzyloxycarbonylerythromycin A 6-carbamate 9-oxime (53)

11-O-(2-Benzoyloxyethoxymethyl)-N-desmethyl-N,2'-O-dibenzyloxycarbonylerythromycin A 6-trichloroacetylcarbamate-4''-formate 9-dibenzyloxycarbonyloxime (52) (487 mg) in methanol (10 ml) was stirred with potassium carbonate (70 mg) at room temperature for 2 h. Water was then added and the mixture was evaporated in vacuo to low bulk, then partitioned between ethyl acetate and water. The solvent layer was dried and evaporated, then the residue was purified by silica gel chromatography eluting with dichloromethane/methanol 100/7 giving the title compound (53) (259 mg 27%) $\nu_{max}$ 3500, 3370, 1725, 1690, 1590 cm$^{-1}$. (Found: MNa$^+$1142, C$_{56}$H$_{85}$N$_3$O$_{20}$ requires MW 1119).

Example 15e

11-O-(2-Hydroxyethoxymethyl)erythromycin A 6-carbamate 9-oxime (54)

11-O-(2-Hydroxyethoxymethyl)-N-desmethyl-N,2'-O-dibenzyloxycarbonylerythromycin A 6-carbamate 9-oxime (53) (211 mg) was treated by the method of Example 1d to give the title compound (54) (143 mg 88%) $\nu_{max}$ (CHCl$_3$) 3500, 3370, 1720, 1585 cm$^{-1}$ [α]$^{20}$ (CHCl$_3$ 1%) −66.4°. (Found: MNa$^+$888, C$_{41}$H$_{75}$N$_3$O$_{16}$ requires MW 865).

Example 16a

11-O-(2-Benzoyloxyethoxymethyl)-N-desmethyl-N,2'-O-dibenzyloxycarbonylerythromycin A 12-carbamate 6-trichloroacetylcarbamate 4''-formate 9-benzyloxycarbonyloxime (55)

11-O-(2-Benzoyloxyethoxymethyl)-N-desmethyl-N,2'-O-dibenzyloxycarbonylerythromycin A 4''-formate (51) (134 mg) in dichloromethane (2 ml) with trichloroacetyl isocyanate (0.2 ml) at room temperature for 1 h. The crude reaction product was then applied to a column of silica gel and eluted with dichloromethane/methanol (100/3). Rechromatography of this product eluting with ethyl acetate/hexane mixtures gave the pure title compound (55) (101 mg, 64%) $\nu_{max}$ (CHCl$_3$) 3500, 3370, 1800, 1730, 1590 cm$^{-1}$.(Found: M−H+2Na$^+$1617, C$_{75}$H$_{95}$Cl$_3$N$_4$O$_{26}$ requires MW 1572).

Example 16b

11-O-(2-Hydroxyethoxymethyl)-N-desmethyl-N,2'-O-dibenzyloxycarbonylerythromycin A 6,12-dicarbamate 9-oxime (56)

11-O-(2-Benzoyloxyethoxymethyl)-N-desmethyl-N,2'-O-dibenzyloxycarbonylerythromycin A 12-carbamate 6-trichloroacetylcarbamate 4''-formate 9-dibenzyloxycarbonyloxime (55) (630 mg) was treated as in Example 15d to give the title compound((295 mg, 63%) after chromatography eluting with dichloromethane/methanol (10/1). $\nu_{max}$ (CHCl$_3$) 3500, 3350, 1730, 1580 cm$^{-1}$. (Found: MNa$^+$1185, C$_{57}$H$_{86}$N$_4$O$_{21}$ requires MW 1162).

Example 16c

11-O-(2-Hydroxyethoxymethyl)erythromycin A 6,12-dicarbamate 9-oxime (57)

11-O-(2-Hydroxyethoxymethyl)-N-desmethyl-N,2'-O-dibenzyloxycarbonylerythromycin A 6,12-dicarbamate 9-oxime (56) (290 mg) was treated by the method of Example 1d to give, after chromatography eluting with dichloro- methane/methanol/0.880 ammonia (100/10/1), the title compound (57) (67 mg, 30%) $\nu_{max}$ (CHCl$_7$) 3500, 3350, 1725, 1590 cm$^{-1}$ [α]$_D^{20}$ (CHCl$_3$ 1%) −64.0°. (Found: MNa$^+$931, C$_{42}$H$_{76}$N$_4$O$_{17}$ requires MW 908).

Example 17a

11-O-(2-Azidoethoxymethyl)-N-desmethyl-N,2'-O-dibenzyloxycarbonylerythromycin A 6-carbamate 9-oxime (58)

11-O-(2-Hydroxyethoxymethyl)-N-desmethyl-N,2'-O-dibenzyloxycarbonylerythromycin A 6-carbamate 9-oxime (53) (455 mg) in tetrahydrofuran (20 ml) was treated with hydrazoic acid in toluene (0.7 ml, 1.7M) and triphenylphosphine (210 mg). Diisopropyl azidodicarboxylate (0.15 ml) was added and the solution was then stirred at room temperature for 30 mins. Ethyl acetate was added and the solution was twice washed with aqueous sodium bicarbonate solution. The organic layer was dried (MgSO$_4$) and evaporated and the residue chromatographed on silica gel, eluting with dichloromethane/diethyl ether (1/1) then with dichloromethane/methanol (100/5) to give the title compound (58) (361 mg, 77%) $\nu_{max}$ (CHCl$_3$) 3500, 3340, 2100, 1720, 1590 cm$^{-1}$. [α]$^{20}$D (CHCl$_3$, 1%) −76.5°. (Found: MNa$^+$1167, C$_{56}$H$_{84}$N$_6$O$_{19}$ requires MW 1144).

Example 17b

11-O-(2-N,N-Dimethylaminoethoxymethyl)erythromycin A 6-carbamate 9-oxime (59)

Treatment of 11-O-(2-azidoethoxymethyl)-N-desmethyl-N,2'-O-dibenzyloxycarbonylerythromycin A 6-carbamate 9-oxime (58) (240 mg) by the method of Example 1d followed by chromatography eluting with dichloromethane/methanol (100/15) gave the title compound (59) (100 mg, 53%) $\nu_{max}$ (CHCl$_3$) 3500, 3360, 1720, 1580 cm$^{-1}$ $[\alpha]^{20}$D (1% wt/vol in CHCl$_3$) -48° (Found: MNa$^+$915, C$_{43}$H$_{80}$N$_4$O$_{15}$ requires MW 892).

Example 17c

11-O-(2-Dimethylaminoethoxymethyl)erythromycin A 6-carbamate (60)

To 11-O-(2-N,N-dimethylaminoethoxymethyl)erythromycin A 6-carbamate 9-oxime (59), (133 mg) in ethanol (5 ml) was added sodium bisulphite (150 mg) in water (5 ml). The mixture was heated to reflux for 30 minutes. The solvent was removed under reduced pressure, and the residue purified by chromatography on silica using 1.5:13:85 NH$_3$:MeOH:CH$_2$Cl$_2$ as eluent, to give the title compound, (60) (40 mg, 30%) as an amorphous solid. $\nu_{max}$(CHCl$_3$) 3500, 3350, 1710, 1580 cm$^{-1}$, $[\alpha]_D^{20}$ (CHCl$_3$, 1%) $-72°$ (Found: MNa$^+$900, C$_{42}$H$_{79}$N$_3$O$_{15}$ requires 877).

Example 18a

11-O-Ethoxymethyl-N-desmethyl-N-2'-O-dibenzyloxycarbonylerythromycin A 9-benzyloxycarbonyloxime (61)

N-Desmethyl-N,2'-O-dibenzyloxycarbonylerythromycin A 9-benzyloxycarbonyloxime (1) (668 mg) in dimethyl formamide (4 ml) was treated with 2,6-lutidine (0.28 ml) and chloromethyl ethyl ether (0.14 ml) and the mixture was stirred 2 h at room temperature. The mixture was worked up as in Example 15a to give the title compound (61) $\nu_{max}$ (CHCl$_3$) 1725, 1690 cm$^{-1}$.

Example 18b

11-O-Ethoxymethyl-N-desmethyl-N,2'-O-dibenzyloxycarbonylerythromycin A 4"-formate 9-benzyloxycarbonyloxime (62)

11-O-Ethoxymethyl-N-desmethyl-N,2'-O-dibenzyloxycarbonylerythromycin A 9-benzyloxycarbonyloxime (61) (164 mg) was formylated by the method of Example 1a to yield the title compound (62) (134 mg, 78%) after chromatography eluting with dichloromethane/methanol (100/3) $\nu_{max}$ (CHCl$_3$) 3500, 1725, 1690, 690 cm$^{-1}$. (Found; MNa$^+$, 1245; C$_{64}$H$_{90}$N$_2$O$_{21}$ requires MW 1222).

Example 18c

11-O-Ethoxymethyl-N-desmethyl-N,2'-O-dibenzyloxycarbonylerythromycin A 6-trichloroacetylcarbamate 4"-formate (63) and 11-O-ethoxymethyl-N-desmethyl-N,2'-O-dibenzyloxycarbonylerythromycin A 12-carbamate 6-trichloroacetylcarbamate-9-benzyloxycarbonyloxime (64)

11-O-Ethoxymethyl-N-desmethyl-N,2'-O-dibenzyloxycarbonylerythromycin A 4"-formate 9-benzyloxycarbonyloxime (62) (1.22 g) in dichloromethane (10 ml) was treated at 0° C. with trichloroacetyl isocyanate (207 mg) in dichloromethane (10 ml). The mixture was stirred at room temperature overnight and was then re-cooled to 0° C. and was again treated with trichloroacetyl isocyanate (95 mg). The reaction mixture was stirred for 1 h at 0° C. and was then worked up as in Example 1b to give a crude product. This was dissolved in methanol/dichloromethane (1/1, 20 ml) and stirred over silica gel (2 g) for 1 h. The solution was filtered and evaporated and the residual oil chromatographed, eluting with dichloromethane/methanol (100/1-100/3). In this way two pure fractions were obtained. The first to be eluted was the 6-trichloroacetylcarbamate (63) (570 mg, 40%) $\nu_{max}$ (CHCl$_3$) 3500, 3400, 1800, 1725, 1690 cm$^{-1}$. (Found: M-H Na$_2^+$1454, C$_{67}$H$_{90}$N$_3$O$_{23}$Cl$_3$ requires MW 1409). The second pure substance to be eluted was the 6-trichloroacetylcarbamate 12-carbamate (64) (320 mg, 22%) $\nu_{max}$(CHCl$_3$) 3500, 3400, 1800, 1720, 1690 cm$^{-1}$. (Found: M-HNa$_2^+$1497, C$_{68}$H$_{91}$N$_4$O$_{24}$Cl$_3$ requires MW 1452).

Example 18d

11-O-Ethoxymethyl-N-desmethyl-N,2'-O-dibenzyloxycarbonylerythromycin A 6-carbamate 9-oxime (65)

11-O-Ethoxymethyl-N-desmethyl-N,2'-O-dibenzyloxycarbonylerythromycin A 6-trichloroacetylcarbamate 4"-formate (63) (690 mg) was hydrolysed by the method of Example 15d and the product chromatographed, eluting with dichloromethane/methanol (100/7) to give the pure title compound (65) (290 mg, 54%) $\nu_{max}$ (CHCl$_3$) 3500, 3400, 1730, 1690, 1590 cm$^{-1}$ (Found: MH$^+$1104, C$_{56}$H$_{85}$N$_3$O$_{19}$ requires 1103).

Example 18e

11-O-Ethoxymethylerythromycin A 6-carbamate 9-oxime (66)

11-O-Ethoxymethyl-N-desmethyl-N,2'-O-dibenzyloxycarbonylerythromycin A 6-carbamate 9-oxime (65) (239 mg) was treated by the method of Example 1d to give the title compound (66) (163 mg, 87%) $\nu_{max}$ (CHCl$_3$) 3500, 3350, 1720, 1590 cm$^{-1}$ $[\alpha]^{20}$D (CHCl$_3$, 1%) $-88.5°$. (Found: MNa$^+$872, C$_{41}$H$_{75}$N$_3$O$_{15}$ requires MW 849).

Example 19a

11-O-Ethoxymethyl-N-desmethyl-N,2'-O-dibenzyloxycarbonylerythromycin A 6,12-dicarbamate 9-oxime (67)

By the method of Example 15d, 11-O-ethoxymethyl-N-desmethyl-N,2'-O-dibenzyloxycarbonylerythromycin A 12-carbamate 6-trichloroacetylcarbamate 9-benzyloxycarbonyloxime (64) (343 mg) was converted to the title compound (67) and purified by silica gel chromatography, eluting with dichloromethane/methanol (100/7) (132 mg, 48%) $\nu_{max}$ $_{(CHCl_3)}$ 3500, 3300, 1730, 1580 cm$^{-1}$ (Found: MH 1147 C$_{57}$H$_{86}$N$_4$O$_{20}$ requires MW 1146).

Example 19b

11-O-Ethoxymethylerythromycin A 6,12-dicarbamate-9-oxime (68)

11-O-Ethoxynethyl-N-desmethyl-N,2'-O-dibenzyloxycarbonylerythromycin A 6,12-dicarbamate 9-oxime (67) (111 mg) was treated by the method of Example 1d to give the title compound (68) (80 mg, 90%) $\nu_{max}$ (CHCl$_3$) 3500, 3350, 1720, 1590 cm$^{-1}$ $[\alpha]_D^{20}$ (CHCl$_3$ %) $-70.3°$. (Found: MNa$^+$915; C$_{42}$H$_{76}$N$_4$O$_{16}$ requires MW 892).

Example 20a

11-O-Ethoxymethyl-N-desmethyl-N,2'-O-dibenzyloxycarbonylerythromycin A 6-carbamate 9-methoxime (69)

11-O-Ethoxymethyl-N-desmethyl-N,2'-O-dibenzyloxy carbonylerythromycin A 6-carbamate 9-oxime (65) (370 mg) in dimethylformamide (3 ml) was treated with iodomethane (0.212 ml) followed by sodium hydride (50% suspension in oil, 19 mg) the mixture being stirred 20 min at room temperature. The product was partitioned between ethyl acetate and water, separating the organic layer, then drying (MgSO$_4$) and evaporating. The residue was chromatographed on silica gel eluting with dichloromethane/methanol (100/5) to give the title compound (69) (255 mg, 67%) $\nu_{max}$ (CHCl$_3$) 3500, 3350, 1725, 1670, 1590 cm$^{-1}$. (Found: MNa+1140, C$_{57}$H$_{87}$N$_3$O$_{19}$ requires MW 1117).

Example 20b

11-O-Ethoxymethylerythromycin A 6-carbamate 9-methoxime (70)

Treatment of 11-O-ethoxymethyl-N-desmethyl-N,2'-O-dibenzyloxycarbonylerythromycin A 6-carbamate 9-methoxime (69) (161 mg) by the method of Example 1d to yield the title compound (70) (105 mg, 84%) $\nu_{max}$ 3500, 3350, 1720, 1590 cm$^{-1}$ [α]$_D^{20}$ (1% in CHCl$_3$) −105.6°. (Found: M+863.5353, C$_{42}$H$_{77}$N$_3$O$_{15}$=863.5354).

Example 21

Erythromycin A 6-p-toluenesulphonylcarbamate 9-methoxime (72)

N-Desmethyl-N,2'-O-dibenzyloxycarbonylerythromycin A 6-p-toluenesulphonylcarbamate 11,4''-diformate 9methoxime (46) (203 mg) was treated by the method of Example 1c and the product [N-desmethyl-N,2'-O-dibenzyloxycarbonylerythromycin A 6-(p toluenesulphonyl)carbamate 9-methoxime, (71)] was isolated by silica gel chromatography eluting with ethyl acetate/hexane (50/50). This product was then treated by the method of Example 1d to give the title compound (72) (117 mg) after chromatography eluting with dichloromethane/methanol/0.880 ammonia (100/10/1) $\nu_{max}$ 3500, 3300, 1750, 1720 cm$^{-1}$ (Found: MH+960, C$_{46}$H$_{77}$N$_3$O$_{16}$ requires MW 959).

I claim:

1. A compountd of the formula I or a pharmaceutically acceptable ester of acid addtion salt thereof:

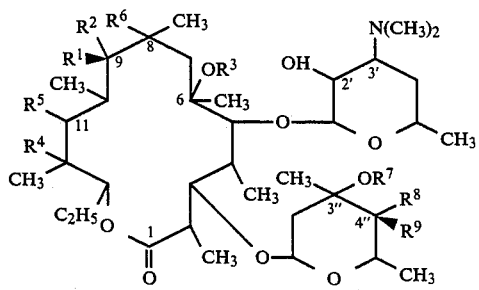

wherein
one of R$^1$ and R$^2$ is hydrogen, and the other of R$^1$ and R$^2$ is amino unsubstitued or substitued by one or two alkyl moieties of 1 to 6 carbon atoms, or the other of R$^1$ and R$^2$ together with R$^5$, is a group of the formula III below, or R$^1$ and R$^2$ together are oxo, oxime unsubstituted or substituted by alkyl, cycloalkyl or alkenyl of up to 6 carbon atoms, phenyl, hydrocarbon-carbonyl or hydrocarbonoxy-carbonyl wherein the gydrocarbon is alkyl of up to 6 carabon atoms or phenyl each of which is unsubstituted or substituted by alkyl of 1 to 6 carbon atoms, heterocyclyl, amino, alkanoylamino of 1 to 6 carbon atoms, mono-, di- or tri-alkylamino of 1 to 6 carbon atoms in each alkyl moiety, hydroxy, alkoxy of 1 to 6 carbon atoms, mercapto, sulphamoyl, carbamoyl, amindino, guanidino, nitro, chloro, bromo, fluoro carboxy or salt or ester thereof, alkanoyloxy of 1 to 6 carbon atoms, arylcarbonyl, heterocyclylcarbonyl or —S(O)$_n$R$^{12}$ wherein n is 0, 1 or 2 and R$^{12}$ is alkyl of 1 to 6 carbon atoms, heterocyclyl or aryl, or an imino; R$^3$ is carbamoyl or N-substituted carbamoyl of the formula —O—CO—NH—X—R$^{15}$ wherein X is —CO— or —SO$_2$— and R$^{15}$ is alkyl of 1 to 6 carbon atoms, haloalkyl of 1 to 6 carbon atoms, alkoxyalkyl of 1 to 6 carbon atoms in each of the alkoxy and alkyl moieties, phenyl, alkylphenyl of 1 to 6 carbon atoms in the alkyl moiety or halophenyl;

R$^4$ is hydrogen or hydroxy, and

R$^5$ is hydroxy, or etherified hydroxy, or R$^5$ together with R$^1$ or R$^2$ is a group of the formula III below as defined above, or R$^4$ and R$^5$ together are a group of the formula II or III:

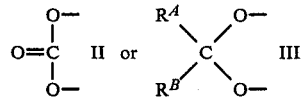

is which

R$^A$ and R$^B$ are the same of different, and each is hydrogen, phenyl, or alkyl of 1 to 6 carbon atoms, said alkyl being unsubstituted or substituted by heterocyclyl, amino, alkanoylamino of 1 to 6 carbon atoms, mono-, di-, or tri-alkylamino of 1 to 6 carbon atoms in each alkyl moiety, hydroxy, alkoxy of 1 to 6 carbon atoms, mercapto, alkylthio of 1 to 6 carbon atoms, heterocyclylthio, arylthio, sulphamoyl, carbamoyl, amidino, guanidino, nitro, chloro, bromo, fluoro, carboxyl or a salt or ester thereof, alkanoyloxy of 1 to 6 carbon atoms, arylcarbonyloxy, heterocyclylcarbonyloxy or acyl;

R$^6$ is hydrogen, fluorine or hydroxy;

R$^7$ is hydrogen or methyl;

one of R$^8$ and R$^9$ is hydrogen, hydroxy, alkoxy, alkanoyloxy, amino, substituted amino of the formula XII or XIII:

   XII

—NHCOR$^{16}$ or

   XIII

—NHSO$_2$R$^{16}$ wherein

R$^{16}$ is alkyl of 1 to 6 carbon atoms or phenyl, unsubstituted or substituted by heterocyclyl, amino, alkanoylamino of 1 to 6 carbon atoms, mono-, di-, or tri-alkylamino of 1 to 6 carbon atoms in each alkyl moiety, hydroxy, alkoxy of 1 to 6 carbon atoms, mercapto, alkylthio of 1 to 6 carbon atoms, heterocyclylthio, arylthio, sulphamoyl, carbamoyl, amidino, guanidino, nitro, chloro, bromo, fluoro, carboxyl or a salt or ester thereof, alkanoyloxy of 1 to 6 carbon atoms, arylcarbonyloxy, heterocyclylcarbonyloxy or acyl, or a group of the formula $R^C SO_2-O-$, in which $R^C$ is, alkyl of 1 to 6 carbon atoms, alkenyl of 2 to 6 carbon atoms, phenyl, nitrophenyl, halophenyl, alkylphenyl of 1 to 6 carbon atoms in the alkyl moiety, benzyl, nitrobenzyl, halobenzyl, alkylbenzyl of 1 to 6 carbon atoms in the alkyl moiety, phenoxyalkyl of 1 to 6 carbon atoms in the alkyl moiety, nitrophenoxyalkyl of 1 to 6 carbon atoms in the alkyl moiety, halophenyoxyalkyl of 1 to 6 carbon atoms in the alkyl moiety, alkylphenoxyalkyl of 1 to 6 carbon atoms in each alkyl moiety or $R^{17}-CH_2-CH_2-$ wherein $R^{17}$ is amino, carbamoyl, sulphamoyl, alkoxy of 1 to 6 carbon atoms, alkylthio of 1 to 6 carbon atoms, aryloxy, arylthio, benzyloxy or benzylthio and the other of $R^8$ and $R^9$ is hydrogen, or $R^8$ and $R^9$ together are oxo, oxime or acetyloxime.

2. A compound according to claim 1, wherein $R^{11}$ is hydrogen or methyl.

3. A compound according to claim 1, wherein $R^4$ is hydroxy.

4. A compound according to claim 1 wherein $R^7$ is methyl.

5. A compound according to claim I wherein $R^8$ is hydrogen and $R^9$ is hydroxy.

6. A compound according to claim 1, wherein $R^5$ is hydroxy.

7. A compound according to claim 1, wherein $R^5$ is alkoxy of 1 to 6 carbon atoms or a group of the formula IX or X:

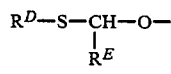   IX

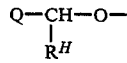   X in which formulae Q is one of the following groups:

   XIA

   XIB

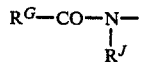   XIC or

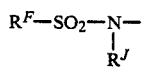   XID $R^D$ is alkyl,
$R^E$ is hydrogen or alkyl of 1 to 6 carbon atoms,
$R^F$ is alkyl of 1 to 6 carbon atoms, alkenyl of 2 to 6 carbon atoms, cycloalkyl of 3 to 7 carbon atoms or phenyl each of which is unsubstituted or substituted by heterocyclyl, amino, alkanoylamino of 1 to 6 carbon atoms, mono-, di-, or tri-alkylamino of 1 to 6 carbon atoms, in each alkyl moiety, hydroxy, alkoxy of 1 to 6 carbon atoms mercapto, alkylthio of 1 to 6 carbon atoms, heterocyclylthio, arylthio, sulphamoyl, carbamoyl, amidino, guanidino, nitro, chloro, bromo, fluoro, carboxyl or a salt or ester thereof, alkanoyloxy of 1 to 6 carbon atoms, arylcarbonyloxy, heterocyclylcarbonyloxy or acyl;

$R^G$ is hydrogen, alkyl of 1 to 6 carbon atoms, alkoxy of 1 to 6 carbon atoms, aryl, aryloxy, cycloalkyl of 3 to 7 carbon atoms or cycloalkyloxy of 3 to 7 carbon atoms unsubstituted or substituted by hydroxy, halo, carboxy, alkoxy of 1 to 6 carbon atoms, aryloxy, formyl, acyloxy, alkoxycarbonyl of 1 to 6 carbon atoms in the alkyl moiety, alkanesulphonyloxy of 1 to 6 carbon atoms in the alkane moiety, trialkylsilyloxy of 1 to 6 carbon atoms in each alkyl moiety, amino, N-alkylamino or N, N-dialkylamino of 1 to 6 carbon atoms in each alkyl moity, oxo, azido, diazo or heterocyclyl, each of $R^H$ and $R^J$, is the same or different, and each is hydrogen or alkyl of up to 6 carbon atoms, cycloalkyl of 3 to 7 carbon atoms or phenyl each of which is unsubstituted or substituted by alkyl of 1 to 6 carbon atoms, heterocyclyl, amino, alkanoylamino of 1 to 6 carbon atoms, mono-, di-, or tri-alkylamino of 1 to 6 carbon atoms in each alkyl moiety, hydroxy, alkoxy of 1 to 6 carbon atoms, mercapto, sulphamoyl, carbamoyl, amidino, guanidino, nitro, chloro, bromo, fluoro, carboxy or salt or ester thereof, alkanoyloxy of 1 to 6 carbon atoms, arylcarbonyl, heterocyclylcarbonyl or $-S(O)_n R^{12}$ wherein n is 0, 1 or 2 and $R^{12}$ is alkyl of 1 to 6 carbon atoms, heterocyclyl or aryl, or any two of $R^F$, $R^G$, $R^H$ and $R^J$ together form a 4- to 7-membered heterocyclic ring together with the intervening atoms of the molecule.

8. The compound according to claim 1, which is (i) erythromycin A 6-carbamate 9-oxime;
(ii) erythromycin A 6-carbamate 9-oxime 11, 12-carbonate;
(iii) erythromycin A 6-carbamate;
(iv) erythromycin A 6,11-dicarbamate 9-methoxime;
(v) erythromycin A 6-carbamate 9-methoxime 11,12-carbonate;
(vi) erythromycin A 6-carbamate 9-imine;
(vii) erythromycylamine 6-carbamate;
(viii) erythromycin A 6-carbamate 11,12-carbonate;
(ix) erythromycin A 6-carbamate 9-methoxime;
(x) erythromycin A 6, 12-dicarbamate 9-methoxime 11-formate;
(xi) erythromycin A 6-carbonate 9-(2-methoxyethoxymethoxime);
(xii) erythromycin A 6-benzoylcarbamate 9-oxime;
(xiii) erythromycin A 6-benzoylcarbamate 9-oxime 11,12-carbonate;
(xiv) erythromycin A 6-benzoylcarbamate 9-methoxime 11,12-carbonate;
(xv) erythromycin A 6-benzoylcarbamate 9-methoxime;
(xvi) erythromycin A 6, 12-bis-acetylcarbamate 9-methoxime 11-formate;
(xvii) erythromycin A 6-acetylcarbamate 9-methoxime 11,12-carbonate;
(xviii) 9-dihydro-9, 11-ethylidene-erythromycin A 6-carbamate;
(xix) erythromycin A 6-methoxyacetylcarbamate 9-methoxime 11,4″-diformate;
(xx) erythromycin A 6,12-methoxyacetylcarbamate 9-methtoxime 11,4″-diformate;
(xxi) erythromycin A 6-p-toluenesulphonylcarbamate 9-methoxime 11,4″-diformate;
(xxii) erythromycin A 6,12-bis-p-toluenesulphonylcarbamate 9-methoxime 11, 4″-diformate;

(xxiii) 11-O-(2-hydroxyethoxymethyl)-erythromycin A 6-carbamate 9-oxime;

(xxiv) 11-O-(2-hydroxyethoxymethyl)-erythromycin A 6,12-dicarbamate 9-oxmine;

(xxv) 11-O-(2-N,N-dimethylaminoethoxymethyl)-erythromycin A 6-carbamate 9-oxime;

(xxvi) 11-O-(2-N,N-dimethylaminoethoxymethyl)-erythromycin A 6-carbamate;

(xxvii) 11-O-ethoxymethyl-erythromycin A 6-carbamate 9-oxime;

(xxviii) 11-O-ethoxymethyl-erythromycin A 6,12-dicarbamate 9-oxime;

(xxix) 11-O-ethoxymethyl-erythromycin A 6-carbamate 9-methoxime; or (xxx) erythromycin A 6-p-toluenesulphonylcarbamate 9-methoxime; or a
pharmaceutically acceptable ester or acid addition salt thereof.

9. A pharmaceutical composition useful for treating bacterial infections in humans and animals which comprises an antibacterially effective amount of the compound of the formula I or a pharmaceutically acceptable ester or acid addition salt thereof:

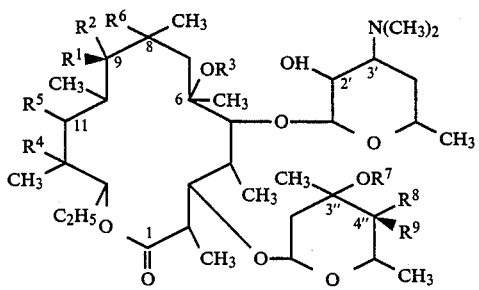

wherein
one of $R^1$ and $R^2$ is hydrogen, and the other of $R^1$ and $R^2$ is amino unsubstituted or substituted by one or two alkyl moieties of 1 to 6 carbon atoms, or the other of $R^1$ and $R^2$, together with $R^5$, is a group of the formula III below, or $R^1$ and $R^2$ together are oxo, oxime unsubstituted or substituted by alky, cycloalkyl or alkenyl of up to 6 carbon atoms, phenyl, hydrocarbon-carbonyl or hydrocarbonoxy-carbonyl wherein the hydrocarbon is alkyl of up to 6 carbon atoms or phenyl each of which is unsubstituted or substituted by alkyl of 1 to 6 carbon atoms, heterocyclyl, amino, alkanoylamino of 1 to 6 carbon atoms, mono-, di- or trialkylamino of 1 to 6 carbon atoms in each alkyl moiety, hydroxy, alkoxy of 1 to 6 carbon atoms, mercapto, sulphamoyl, carbamoyl, amidino, guanidino, nitro, chloro, bromo, fluoro, carboxy or salt or ester thereof, alkanoyloxy of 1 to 6 carbon atoms, arylcarbonyl, heterocyclylcarbonyl or $-S(O)_nR^{12}$ wherein n is 0, 1 or 2 and $R^{12}$ is alkyl of 1 to 6 carbon atoms, heterocyclyl or aryl, or an imino; $R^3$ is carbamoyl or N-substituted carbamoyl of the formula $-O-CO-NH-X-R^{15}$ wherein X is $-CO-$ or $-SO_2$ and $R^{15}$ is alkyl of 1 to 6 carbon atoms, haloalkyl of 1 to 6 carbon atoms, alkoxyalkyl of 1 to 6 carbon atoms in each of the alkoxy and alkyl moieties, phenyl, alkylphenyl of 1 to 6 carbon atoms in the alkyl moiety or halophenyl;

$R^4$ is hydrogen or hydroxy, and $R^5$ is hydroxy, or etherified hydroxy, or $R^5$ together with $R^1$ or $R^2$ is a group of the formula III below as defined above, or $R^4$ and $R^5$ together are a group of the formula II or III:

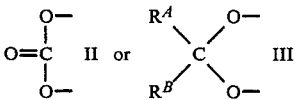

in which
$R^A$ and $R^B$ are the same or different, and each is hydrogen, phenyl, or alkyl of 1 to 6 carbon atoms, said alkyl being unsubstituted or substituted by heterocyclyl, amino, alkanoylamino of 1 to 6 carbon atoms, mono-, di-, or tri-alkylamino of 1 to 6 carbon atoms in each alkyl moiety, hydroxy, alkoxy of 1 to 6 carbon atoms, mercapto, alkylthio of 1 to 6 carbon atoms, heterocyclylthio, arylthio, sulphamoyl, carbamoyl, amidino, guanidino, nitro, chloro, bromo, fluoro, carboxyl or a salt or ester thereof, alkanoyloxy of 1 to 6 carbon atoms, arylcarbonyloxy, heterocyclylcarbonyloxy or acyl;

$R^6$ is hydrogen, fluorine or hydroxy;

$R^7$ is hydrogen or methyl;

one of $R^8$ and $R^9$ is hydrogen, hydroxy, alkoxy, alkanoyloxy, amino, substituted amino of the formula XII or XIII:

$$-NHCOR^{16} \qquad \text{XII}$$

or $$-NHSO_2R^{16} \qquad \text{XIII}$$

wherein
$R^{16}$ is alkyl of 1 to 6 carbon atoms or phenyl, unsubstituted or substituted by heterocyclyl, amino, alkanoylamino of 1 to 6 carbon atoms, mono-, di-, or tri-alkylamino of 1 to 6 carbon atoms in each alkyl moiety, hydroxy, alkoxy of 1 to 6 carbon atoms, mercapto, alkylthio of 1 to 6 carbon atoms, heterocyclylthio, arylthio, sulphamoyl, carbamoyl, amidino, guanidino, nitro, chloro, bromo, fluoro, carboxyl or a salt or ester thereof, alkanoyloxy of 1 to 6 carbon atoms, arylcarbonyloxy, heterocyclylcarbonyloxy or acyl, or a group of the formula $R^CSO_2-O-$, in which $R^C$ is, alkyl of 1 to 6 carbon atoms, alkenyl of 2 to 6 carbon atoms, phenyl, nitrophenyl, halophenyl, alkylphenyl of 1 to 6 carbon atoms in the alkyl moiety, benzyl, nitrobenzyl, halobenzyl, alkylbenzyl of 1 to 6 carbon atoms in the alkyl moiety, phenoxyalkyl of 1 to 6 carbon atoms in the alkyl moiety, nitrophenoxyalkyl of 1 to 6 carbon atoms in the alkyl moiety, halophenyoxyalkyl of 1 to 6 carbon atoms in the alkyl moiety, alkylphenoxyalkyl of 1 to 6 carbon atoms in the alkyl moiety or $R^{17}-CH_2-CH_2-$ wherein $R^{17}$ is amino, carbamoyl, sulphamoyl, alkoxy of 1 to 6 carbon atoms, alkylthio of 1 to 6 carbon atoms, aryloxy, arylthio, benzyloxy or benzylthio and the other of $R^8$ and $R^9$ is hydrogen, or $R^8$ and $R^9$ together are oxo, oxime or acetyloxime, in combination with a pharmaceutically acceptable carrier.

10. A composition according to claim 9, wherein $R^{11}$ is hydrogen or methyl.

11. A composition according to claim 9, wherein $R^4$ is hydroxy.

12. A composition according to claim 9 wherein $R^7$ is methyl.

13. A composition according to claim 9 wherein $R^8$ is hydrogen and $R^9$ is hydroxy.

14. A composition according to claim 9, wherein $R^5$ is hydroxy.

15. A composition according to claim 9, wherein $R^5$ is alkoxy of 1 to 6 carbon atoms or a group of the formula IX or X:

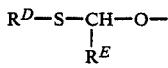       IX

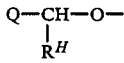       X in which formulae Q is one of the following groups:

       XIA

       XIB

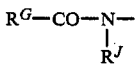       XIC or

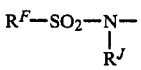       XID $R^D$ is alkyl,
$R^E$ is hydrogen or alkyl of 1 to 6 carbon atoms,
$R^F$ is alkyl of 1 to 6 carbon atoms, alkenyl of 2 to 6 carbon atoms, cycloalkyl of 3 to 7 carbon atoms or phenyl each of which is unsubstituted or substituted by heterocyclyl, amino, alkanoylamino of 1 to 6 carbon atoms, mon-, di-, or tri-alkylamino or 1 to 6 carbon atoms in each alkyl moiety, hydroxy, alkoxy of 1 to 6 carbon atoms, mercapato, alkylthio of 1 to 6 carbon atoms, heterocyclylthio, arylthio, sulphamoyl, carbamoyl, amidino, guanidino, nitro, chloro, bromo, fluoro, carboxyl or a salt or ester thereof, alkanoyloxy of 1 to 6 carbon atoms, arylcarbonyloxy, heterocyclylcarbonyloxy or acyl;
$R^G$ is hydrogen, alkyl of 1 to 6 carbon atoms, alkoxy of 1 to 6 carbon atoms, aryl, aryloxy, cycloalkyl of 3 to 7 carbon atoms or cycloalkyloxy of 3 to 7 carbon atoms unsubstituted or substituted by hydroxy, halo, carboxy, alkoxy of 1 to 6 carbon atoms, aryloxy, formyl, acyloxy, alkoxycarbonyl of 1 to 6 carbon atoms in the alkyl moiety, alkanesulphonyloxy of 1 to 6 carbon atoms in the alkane moiety, trialkylsilyloxy of 1 to 6 carbon atoms in each alkyl moiety, amino, N-alkylamino or N,N-dialkylamino of 1 to 6 carbon atoms in each alkyl moiety, oxo, azido, diazo or heterocyclyl, each of $R^H$ and $R^J$, is the same or different, and each is hydrogen or alkyl of up to 6 carbon atoms, cycloalkyl of 3 to 7 carbon atoms or phenyl each of which is unsubstituted or substituted by alkyl of 1 to 6 carbon atoms, heterocyclyl, amino, alkanoylamino of 1 to 6 carbon atoms, mono-, di- or tri-alkylamino of 1 to 6 carbon atoms in each alkyl moiety, hydroxy, alkoxy of 1 to 6 carbon atoms, mercapto, sulphamoyl, carbamoyl, amidino, guanidino, nitro, chloro, bromo, fluoro, carboxy or salt or ester thereof, alkanoyloxy of 1 to 6 carbon atoms, arylcarbonyl, heterocyclylcarbonyl or $-S(O)_nR^{12}$ wherein n is 0, 1 or 2 and $R^{12}$ is alkyl of 1 to 6 carbon atoms, heterocyclyl or aryl, or any two of $R^F$, $R^G$, $R^H$ and $R^J$ together form a 4- to 7-membered heterocyclic ring together with the intervening atoms of the molecule.

16. The composition according to claim 9, wherein the compound of formula I is
(i) erythromycin A 6-carbamate 9-oxime;
(ii) erythromycin A 6-carbamate 9-oxime 11, 12-carbonate;
(iii) erythromycin A 6-carbamate;
(iv) erythromycin A 6,11-dicarbamate 9-methoxime;
(v) erythromycin A 6-carbamate 9-methoxime 11,12-carbonate;
(vi) erythromycin A 6-carbamate 9-imine;
(vii) erythromycylamine 6-carbamate,
(viii) erythromycin A 6-carbamate 11,12-carbonate;
(ix) erythromycin A 6-carbamate 9-methoxime;
(x) erythromycin A 6,12-dicarbamate 9-methoxime 11-formate;
(xi) erythromycin A 6-carbamate 9-(2-methoxyethoxymethoxime);
(xii) erythromycin A 6-benzoylcarbamate 9-oxime;
(xiii) erythromycin A 6-benzoylcarbamate 9-oxime 11,12-carbonate;
(xiv) erythromycin A 6-benzoylcarbamate 9-methoxime 11,12-carbonate;
(xv) erythromycin A 6-benzoylcarbamate 9-methoxime;
(xvi) erythromycin A 6,12-bis-acetylcarbamate 9-methoxime 11-formate;
(xvii) erythromycin A 6-acetylcarbamate 9-methoxime 11,12-carbonate;
(xviii) 9-dihydro-9, 11-ethylidene-erythromycin A 6-carbamate;
(xix) erythromycin A 6-methoxyacetylcarbamate 9-methoxime 11, 4″-diformate;
(xx) erythromycin A 6,12-methoxyacetylcarbamate 9-methoxime 11,4″-diformate;
(xxi) erythromycin A 6-p-toluenesulphonylcarbamate 9-methoxime 11,4″-diformate;
(xxii) erythromycin A 6,12-bis-p-toluenesulphonylcarbamate 9-methoxime 11,4″-diformate;
(xxiii) 11-O-(2-hydroxyethoxymethyl)-erythromycin A 6-carbamate 9-oxime;
(xxiv) 11-O-(2-hydroxyethoxymethyl)-erythromycin A 6, 12-dicarbamate 9-oxime;
(xxv) 11-O-(2-N, N-dimethylaminoethoxymethyl)-erythromycin A 6-carbamate 9-oxime;
(xxvi) 11-O-(2-N, N-dimethylaminoethoxymethyl)-erythromycin A 6 -carbamate;
(xxvii) 11-O-ethoxymethyl-erythromycin A 6-carbamate 9-oxime;
(xxviii) 11-O-ethoxymethyl-erythromycin A 6,12-dicarbamate 9-oxime;
(xxix) 1-O-ethoxymethyl-erythromycin A 6-carbamate 9-methoxime; or
(xxx) erythromycin A 6-p-toluenesulphonylcarbamate 9-methoxime; or a
pharmaceutically acceptable ester or acid addition salt thereof.

17. A method of treating bacterial infections in humans and animals which comprises administering to a human or animal in need thereof an antibacterially effective amount of the compound of the formula I or a pharmaceutically acceptable ester or acid addition salt thereof:

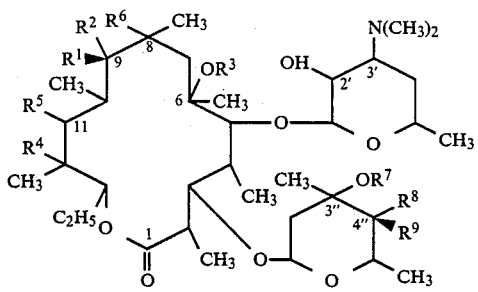

wherein
one of $R^1$ and $R^2$ is hydrogen, and the other of $R^1$ and $R^2$ is amino unsubstituted or substituted by one or two alkyl moieties of 1 to 6 carbon atoms, or the other of $R^1$ and $R^2$, together with $R^5$, is a group of the formula III below, or $R^1$ and $R^2$ together are oxo, oxime unsubstituted or substituted by alkyl, cycloalkyl or alkenyl of up to 6 carbon atoms, phenyl, hydrocarbon-carbonyl or hydrocarbonoxy-carbonyl wherein the hydrocarbon is alkyl of up to 6 carbon atoms or phenyl each of which is unsubstituted or substituted by alkyl of 1 to 6 carbon atoms, heterocyclyl, amino, alkanoylamino of 1 to 6 carbon atoms, mono-, di- or tri-alkylamino of 1 to 6 carbon atom in each alkyl moiey, hydroxy, alkoxy of 1 to 6 carbon atoms, mercapto, sulphamoyl, carbamoyl, amidino, guanidino, nitro, chloro, bromo, fluoro, carboxy or salt or ester thereof, alkanoyloxy of 1 to 6 carbon atoms, arylcarbonyl, heterocyclylcarbonyl or —S(O)$_n$R$^{12}$ wherein n is 0, 1 or 2 and $R^{12}$ is alkyl of 1 to 6 carbon atoms, heterocyclyl or aryl, or an imino; $R^3$ is carbamoyl or N-substituted carbamoyl of the formula —O—CO—NH—X—R$^{15}$ wherein X is —CO— or —SO$_2$ and $R^{15}$ is alkyl of 1 to 6 carbon atoms, haloalkyl of 1 to 6 carbon atoms, alkoxyalkyl of 1 to 6 carbon atoms in each of the alkoxy and alkyl moieties, phenyl, alkylphenyl of 1 to 6 carbon atoms in the alkyl moiety or halophenyl;
$R^4$ is hydrogen or hydroxy, and
$R^5$ is hydroxy, or etherified hydroxy, or $R^5$ together with $R^1$ or
$R^2$ is a group of the formula III below as defined above, or
$R^4$ and $R^5$ together are a group of the formula II or III:

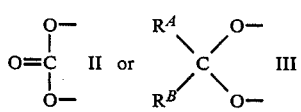

in which
$R^A$ and $R^B$ are the same or different, and each is hydrogen, phenyl, or alkyl of 1 to 6 carbon atoms, said alkyl being unsubstituted or substituted by heterocyclyl, amino, alkanoylamino of 1 to 6 carbon atoms, mono-, di-, or tri-alkylamino of 1 to 6 carbon atoms in each alkyl moiety, hydroxy, alkoxy of 1 to 6 carbon atoms, mercapto, alkylthio of 1 to 6 carbon atoms, heterocyclylthio, arylthio, sulphamoyl, carbamoyl, amidino, guanidino, nitro, chloro, bromo, fluoro, carboxyl or a salt or ester thereof, alkanoyloxy of 1 to 6 carbon atoms, arylcarbonyloxy, heterocyclylcarbonyloxy or acyl;
$R^6$ is hydrogen, fluorine or hydroxy;
$R^7$ is hydrogen or methyl;
one of $R^8$ and $R^9$ is hydrogen, hydroxy, alkoxy, alkanoyloxy, amino, substituted amino of the formula XII or XIII:

$$-NHCOR^{16} \qquad XII$$

or $$-NHSO_2R^{16} \qquad XIII$$

wherein
$R^{16}$ is alkyl of 1 to 6 carbon atoms or phenyl, unsubstituted or substituted by heterocyclyl, amino, alkanoylamino of 1 to 6 carbon atoms, mono-, di-, or tri-alkylamino of 1 to 6 carbon atoms in each alkyl moiety, hydroxy, alkoxy of 1 to 6 carbon atoms, mercapto, alkylthio of 1 to 6 carbon atoms, heterocyclylthio, arylthio, sulphamoyl, carbamoyl, amidino, guanidino, nitro, chloro, bromo, fluoro, carboxyl or a salt or ester thereof, alkanoyloxy of 1 to 6 carbon atoms, arylcarbonyloxy, heterocyclylcarbonyloxy or acyl, or a group of the formula $R^CSO_2$—O—, in which $R^C$ is, alkyl of 1 to 6 carbon atoms, alkenyl of 2 to 6 carbon atoms, phenyl, nitrophenyl, halophenyl, alkylphenyl of 1 to 6 carbon atoms in the alkyl moiety, benzyl, nitrobenzyl, halobenzyl, alkylbenzyl of 1 to 6 carbon atoms in the alkyl moiety, phenoxyalkyl of 1 to 6 carbon atoms in the alkyl moiety, nitrophenoxyalkyl of 1 to 6 carbon atoms in the alkyl moiety, halophenyoxyalkyl of 1 to 6 carbon atoms in the alkyl moiety, alkylphenoxyalkyl of 1 to 6 carbon atoms in each alkyl moiety or $R^{17}$—CH$_2$—CH$_2$— wherein $R^{17}$ is amino, carbamoyl, sulphamoyl, alkoxy of 1 to 6 carabon atoms, alkylthio of 1 to 6 carbon atoms, aryloxy, arylthio, benzyloxy or benzylthio and the other of $R^8$ and $R^9$ is hydrogen, or $R^8$ and $R^9$ together are oxo, oxime or acetyloxime, in combination with a pharmaceutically acceptable carrier.

18. A method according to claim 17, wherein $R^{11}$ is hydrogen or methyl.

19. A method according to claim 17, wherein $R^4$ is hydroxy.

20. A method according to claim 17, wherein $R^7$ is methyl.

21. A method accroding to claim 17 wherein $R^8$ is hydrogen and $R^9$ is hydroxy.

22. A method according to claim 17, wherein $R^5$ is hydroxy.

23. A method according to claim 17, wherein $R^5$ is alkoxy of 1 to 6 carbon atoms or a group of the formula IX or X:

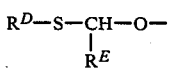

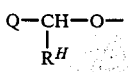

in which formulae Q is one of the following groups:

$R^F\!-\!O\!-\!$        XIA $R^G\!-\!CO\!-\!O\!-\!$        XIB $R^G\!-\!CO\!-\!\underset{\underset{R^J}{|}}{N}\!-\!$        XIC or $R^F\!-\!SO_2\!-\!\underset{\underset{R^J}{|}}{N}\!-\!$        XID $R^D$ is alkyl, $R^E$ is hydrogen or alkyl of 1 to 6 carbon atoms, $R^F$ is alkyl of 1 to 6 carbon atoms, alkenyl of 2 to 6 carbon atoms, cycloalkyl of 3 to 7 carbon atoms or phenyl each of which is unsubstituted or substituted by heterocyclyl, amino, alkanoylamino of 1 to 6 carbon atoms, mono-, di- or tri-alkylamino of 1 to 6 carbon atoms in each alkyl moiety, hydroxy, alkoxy of 1 to 6 carbon atoms, mercapto, alkylthio of 1 to 6 carbon atoms, heterocyclylthio, arylthio, sulphamoyl, carbamoyl, amidino, guanidino, nitro, chloro, bromo, fluoro, carboxyl or a salt or ester thereof, alkanoyloxy of 1 to 6 carbon atoms, arylcarbonyloxy, heterocyclylcarbonyloxy or acyl;

$R^G$ is hydrogen, alkyl of 1 to 6 carbon atoms, alkoxy of 1 to 6 carbon atoms, aryl, aryloxy, cycloalkyl of 3 to 7 carbon atoms or cycloalkyloxy of 3 to 7 carbon atoms unsubstituted or substituted by hydroxy, halo, carboxy, alkoxy of 1 to 6 carbon atoms, aryloxy, formyl, acyloxy, alkoxycarbonyl of 1 to 6 carbon atoms in the alkyl moiety, alkanesulphonyloxy of 1 to 6 carbon atoms in the alkane moiety, trialkylsilyloxy of 1 to 6 carbon atoms in each alkyl moiety, amino, N-alkylamino or N, N-dialkylamino of 1 to 6 carbon atoms in each alkyl moiety, oxo, azido, diazo or heterocyclyl, each of $R^H$ and $R^J$, is the same or different, and each is hydrogen or alkyl of up to 6 carbon atoms, cycloalkyl of 3 to 7 carbon atoms or phenyl each of which is unsubstituted or substituted by alkyl of 1 to 6 carbon atoms, heterocyclyl, amino, alkanoylamino of 1 to 6 carbon atoms, mono-, di- or tri-alkylamino of 1 to 6 carbon atoms in each alkyl moiety, hydroxy, alkoxy of 1 to 6 carbon atoms, mercapto, sulphamoyl, carbamoyl, amidino, guanidino, nitro, chloro, bromo, fluoro, carboxy or salt or ester thereof, alkanoyloxy of 1 to 6 carbon atoms, arylcarbonyl, heterocyclylcarbonyl or $-S_{(O)_n}R^{12}$ wherein n is 0,1 or 2 and $R_{12}$ is alkyl of 1 to 6 carbon atoms, heterocyclyl or aryl, or any two of $R^F$, $R^G$, $R^H$ and $R^J$ together form a 4- to 7-membered heterocyclic ring together with the intervening atoms of the molecule.

24. The method according to claim 17, wherein the compound of formula I is (i) erythromycin A 6-carbamate 9-oxime;
(ii) erythromycin A 6-carbamate 9-oxime 11,12-carbonate;
(iii) erythromycin A 6-carbamate;
(iv) erythromycin A 6,11-dicarbamate 9-methoxime;
(v) erythromycin A 6-carbamate 9-methoxime 11,12-carbonate;
(vi) erythromycin A 6-dicarbamate 9-imine;
(vii) erythromycylamine 6-carbamate;
(viii) erythromycin A 6-carbamate 11, 12-carbonate;
(ix) erythromycin A 6-carbamate 9-methoxime
(x) erythromycin A 6, 12-dicarbamate 9-methoxime 11-formate;
(xi) erythromycin A 6-carbamate 9-(2-methoxy- ethoxymethoxime);
(xii) erythromycin A 6-benzoylcarbamate 9-oxime;
(xiii) erythromycin A 6-benzoylcarbamate 9-oxime 11,12-carbonate;
(xiv) erythromycin A 6-benzoylcarbamate 9-methoxime 11,12-carbonate;
(xv) erythromycin A 6-benzoylcarbamate 9-methoxime;
(xvi) erythromycin A 6, 12-bis-acetylcarbamate 9-methoxime 11-formate;
(xvii) erythromycin A 6-acetylcarbamate 9-methoxime 11,12-carbonate;
(xviii) 9-dihydro-9,11-ethylidene-erythromycin A 6-carbamate;
(xix) erythromycin A 6-methoxyacetylcarbamate 9methoxime 11,4''-diformate;
(xx) erythromycin A 6,12-methoxyacetylcarbamate 9-methoxime 11,4''-diformate;
(xxi) erythromycin A 6-p-toluenesulphonylcarbamate 9-methoxime 11,4''-diformate;
(xxii) erythromycin A 6,12-bis-p-toluenesulphonylcarbamate 9-methoxime 11, 4''-diformate;
(xxiii) 11-O-(2-hydroxyethoxymethyl)-erythromycin A 6-carbamate 9-oxime;
(xxiv) 11-O-(2-hydroxyethoxymethyl)-erythromycin A 6,12-dicarbamate 9-oxime;
(xxv) 11-O-(2-N, N-dimethylaminoethoxymethyl)-erythromycin A 6-carbamate 9-oxime;
(xxvi) 11-O-(2-N, N-dimethylaminoethoxymethyl)-erythromycin A 6-carbamate;
(xxvii) 11-O-ethoxymethyl-erythromycin A 6-carbamate 9-oxime;
(xxviii) 11-O-ethoxymethyl-erythromycin A 6,12-dicarbamate 9-oxime;
(xxix) 1-O-ethoxymethyl-erythromycin A 6-carbamate 9-methoxime; or
(xxx) erythromycin A 6-p-toluenesulphonylcarbamate 9-methoxime; or a pharaceutically acceptable ester or acid addtion salt thereof.

* * * * *